United States Patent
Lange et al.

(10) Patent No.: US 12,054,552 B2
(45) Date of Patent: Aug. 6, 2024

(54) HUMANIZED ANTI-IL-1R3 ANTIBODY AND METHODS OF USE

(71) Applicant: SANOFI BIOTECHNOLOGY, Gentilly (FR)

(72) Inventors: Christian Lange, Frankfurt am Main (DE); Ziyu Li, Frankfurt am Main (DE); Björn Steinmann, Frankfurt am Main (DE); Hanno Sjuts, Frankfurt am Main (DE); Sandra Weil, Frankfurt am Main (DE)

(73) Assignee: SANOFI BIOTECHNOLOGY, Gentilly (FR)

( * ) Notice: Subject to any disclaimer, the term of this patent is extended or adjusted under 35 U.S.C. 154(b) by 0 days.

(21) Appl. No.: 18/471,388

(22) Filed: Sep. 21, 2023

(65) Prior Publication Data

US 2024/0101691 A1   Mar. 28, 2024

(51) Int. Cl.
  *C07K 16/28*   (2006.01)
  *A61P 35/00*   (2006.01)

(52) U.S. Cl.
  CPC .......... *C07K 16/2866* (2013.01); *A61P 35/00* (2018.01)

(58) Field of Classification Search
  CPC .................................. C07K 16/2866
  USPC ........................................ 424/172.1
  See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,108,921 A | 4/1992 | Low et al. | |
| 5,149,782 A | 9/1992 | Chang et al. | |
| 5,202,238 A | 4/1993 | Fell, Jr. et al. | |
| 5,204,244 A | 4/1993 | Fell et al. | |
| 5,225,539 A | 7/1993 | Winter | |
| 5,283,179 A | 2/1994 | Wood | |
| 5,429,746 A | 7/1995 | Shadle et al. | |
| 5,641,641 A | 6/1997 | Wood | |
| 5,648,260 A | 7/1997 | Winter et al. | |
| 5,650,289 A | 7/1997 | Wood | |
| 5,739,277 A | 4/1998 | Presta et al. | |
| 5,834,250 A | 11/1998 | Wells et al. | |
| 5,869,046 A | 2/1999 | Presta et al. | |
| 6,096,871 A | 8/2000 | Presta et al. | |
| 6,121,022 A | 9/2000 | Presta et al. | |
| 6,194,551 B1 | 2/2001 | Idusogie et al. | |
| 6,242,195 B1 | 6/2001 | Idusogie et al. | |
| 6,277,375 B1 | 8/2001 | Ward | |
| 6,280,955 B1 | 8/2001 | Cao | |
| 6,528,624 B1 | 3/2003 | Idusogie et al. | |
| 6,538,124 B1 | 3/2003 | Idusogie et al. | |
| 6,586,207 B2 | 7/2003 | Tirrell et al. | |
| 6,602,684 B1 | 8/2003 | Umana et al. | |
| 6,737,056 B1 | 5/2004 | Presta | |
| 6,821,505 B2 | 11/2004 | Ward | |
| 6,998,253 B1 | 2/2006 | Presta et al. | |
| 7,083,784 B2 | 8/2006 | Dall'Acqua et al. | |
| 7,390,880 B2 | 6/2008 | Bednarik et al. | |
| 9,796,783 B2 | 10/2017 | Ågerstam | |
| 10,906,971 B2 | 2/2021 | Fischer et al. | |
| 11,198,728 B2 | 12/2021 | Fischer et al. | |
| 11,203,642 B2 | 12/2021 | Fischer et al. | |
| 11,639,392 B2 | 5/2023 | Fischer et al. | |
| 2003/0026806 A1 | 2/2003 | Witte et al. | |
| 2004/0214988 A1 | 10/2004 | Tirrell et al. | |
| 2012/0251531 A1 | 10/2012 | Baehner et al. | |
| 2014/0017167 A1 | 1/2014 | Fioretos et al. | |
| 2015/0315179 A1 | 11/2015 | Jiang et al. | |
| 2017/0121420 A1 | 5/2017 | Heidrich et al. | |
| 2019/0106487 A1 | 4/2019 | Fischer et al. | |
| 2019/0194336 A1* | 6/2019 | Fischer | A61P 43/00 |
| 2020/0048349 A1 | 2/2020 | Gaudet et al. | |
| 2020/0140559 A1 | 5/2020 | Fischer et al. | |
| 2020/0407438 A1 | 12/2020 | Fischer et al. | |
| 2022/0089751 A1 | 3/2022 | Fischer et al. | |
| 2022/0169718 A1 | 6/2022 | Fischer et al. | |

FOREIGN PATENT DOCUMENTS

| | | |
|---|---|---|
| CN | 1934072 A | 3/2007 |
| CN | 102939304 A | 2/2013 |
| EP | 0120694 A2 | 10/1984 |
| EP | 0125023 A1 | 11/1984 |
| EP | 0239400 A2 | 9/1987 |
| EP | 0488470 A1 | 6/1992 |
| EP | 0519596 A1 | 12/1992 |

(Continued)

OTHER PUBLICATIONS

Reinhart et al (Biotechnology Journal, 2019, 14 (1700686): 1-11).*
Angal et al., A single amino acid substitution abolishes the heterogeneity of chimeric mouse/human (IgG4) antibody, Mol Immunol. Jan. 1993, 30(1): 105-108.
Labrijn et al., Species-specific determinants in the IgG CH3 domain enable Fab-arm exchange by affecting the noncovalent CH3—CH3 interaction strength, J. Immunol., 2011, 187: 3238-3246.
Parekh et al., Development and validation of an antibody-dependent cell-mediated cytotoxicity-reporter gene assay, MAbs, May-Jun. 2012, 4(3): 310-318, Epub Apr. 26, 2012.

(Continued)

*Primary Examiner* — Sean E Aeder
(74) *Attorney, Agent, or Firm* — LATHROP GPM LLP; James H. Velema, Esq.; Michael J. Spellberg

(57) ABSTRACT

An antibody that specifically binds to IL-1R3, comprising an antibody heavy chain amino acid sequence of SEQ ID NO: 1 and a light chain amino acid sequence of SEQ ID NO: 2. A pharmaceutical composition is provided comprising the said antibody and a pharmaceutically acceptable diluent, carrier or excipient. Also said antibody for use in treating a disease or disorder in a subject in need thereof. The disease or disorder may be an autoimmune or autoinflammatory disease or disorder.

22 Claims, 6 Drawing Sheets

Specification includes a Sequence Listing.

(56) References Cited

FOREIGN PATENT DOCUMENTS

| | | |
|---|---|---|
| EP | 0194276 B2 | 1/2002 |
| EP | 1255780 A1 | 11/2002 |
| EP | 1633787 A1 | 3/2006 |
| JP | 2014-511348 A | 5/2014 |
| WO | WO 1986/001533 A1 | 3/1986 |
| WO | WO 1988/007089 A1 | 9/1988 |
| WO | WO 1996/014339 A1 | 5/1996 |
| WO | WO 1996/023067 A1 | 8/1996 |
| WO | WO 1997/037016 A1 | 10/1997 |
| WO | WO 1998/005787 A1 | 2/1998 |
| WO | WO 1998/023289 A1 | 6/1998 |
| WO | WO 1998/048032 A2 | 10/1998 |
| WO | WO 1999/051642 A1 | 10/1999 |
| WO | WO 1999/058572 A1 | 11/1999 |
| WO | WO 2000/009560 A2 | 2/2000 |
| WO | WO 2000/032767 A1 | 6/2000 |
| WO | WO 2000/042072 A2 | 7/2000 |
| WO | WO 2001/055216 A1 | 8/2001 |
| WO | WO 2002/044215 A2 | 6/2002 |
| WO | WO 2002/060919 A2 | 8/2002 |
| WO | WO 2002/064630 A2 | 8/2002 |
| WO | WO 2003/014309 A2 | 2/2003 |
| WO | WO 2002/064630 A3 | 8/2003 |
| WO | WO 2003/073238 A2 | 9/2003 |
| WO | WO 2003/074569 A2 | 9/2003 |
| WO | WO 2004/009823 A1 | 1/2004 |
| WO | WO 2004/016750 A2 | 2/2004 |
| WO | WO 2004/022718 A2 | 3/2004 |
| WO | WO 2004/029207 A2 | 4/2004 |
| WO | WO 2004/035752 A2 | 4/2004 |
| WO | WO 2004/063351 A2 | 7/2004 |
| WO | WO 2004/065540 A2 | 8/2004 |
| WO | WO 2004/074455 A2 | 9/2004 |
| WO | WO 2004/099249 A2 | 11/2004 |
| WO | WO 2004/100987 A2 | 11/2004 |
| WO | WO 2004/106377 A1 | 12/2004 |
| WO | WO 2005/035727 A2 | 4/2005 |
| WO | WO 2005/040217 A2 | 5/2005 |
| WO | WO 2005/044859 A2 | 5/2005 |
| WO | WO 2005/070963 A1 | 8/2005 |
| WO | WO 2005/073164 A1 | 8/2005 |
| WO | WO 2005/074524 A2 | 8/2005 |
| WO | WO 2005/077981 A2 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/085967 A2 | 8/2006 |
| WO | WO 2007/003041 A1 | 1/2007 |
| WO | WO 2007/031875 A2 | 3/2007 |
| WO | WO 2008/045140 A1 | 4/2008 |
| WO | WO 2009/120903 A2 | 10/2009 |
| WO | WO 2010/108127 A1 | 9/2010 |
| WO | WO 2011/021014 A2 | 2/2011 |
| WO | WO 2011/124718 A1 | 10/2011 |
| WO | WO 2011/147903 A1 | 12/2011 |
| WO | WO 2012/098407 A1 | 7/2012 |
| WO | WO 2012/142391 A1 | 10/2012 |
| WO | WO 2012/177595 A1 | 12/2012 |
| WO | WO 2013/023015 A2 | 2/2013 |
| WO | WO 2013/165894 A2 | 11/2013 |
| WO | WO 2013/165894 A3 | 11/2013 |
| WO | WO 2014/100772 A1 | 6/2014 |
| WO | WO 2014/113433 A1 | 7/2014 |
| WO | WO 2015/132602 A1 | 9/2015 |
| WO | WO 2016/020502 A1 | 2/2016 |
| WO | WO 2016/207304 A2 | 12/2016 |
| WO | WO 2017/191325 A1 | 11/2017 |
| WO | WO 2018/206565 A9 * | 11/2018 |
| WO | WO 2018/231827 A9 * | 12/2018 |
| WO | WO 2022/053715 A1 | 3/2022 |
| WO | WO 2022/136569 A1 | 6/2022 |
| WO | WO 2022/170008 A2 | 8/2022 |
| WO | WO 2022/243536 A1 | 11/2022 |

OTHER PUBLICATIONS

Silva et al., The S228P mutation prevents in vivo and in vitro IgG4 Fab-arm exchange as demonstrated using a combination of novel quantitative immunoassays and physiological matrix preparation, J Biol Chem., Feb. 27, 2015, 290(9): 5462-5469, Epub Jan. 7, 2015.

Armour, et al., "Recombinant human IgG molecules lacking Fcg receptor I binding and monocyte triggering activities", European Journal of Immunology 29(8): 2613-2624 (Aug. 1, 1999).

Backliwal, et al., Rational Vector Design and Multi-Pathway Modulation of Hek 293e Cells Yield Recombinant Antibody Titers Exceeding 1 G/L by Transient Transfection Under Serum-Free Conditions, Nucleic Acids Research, vol. 36 Issue 15, pp. e96, Sep. 1, 2008.

Chenoweth et al., Harnessing the immune system via FcγR function in immune therapy: a pathway to next-gen mAbs, Immunol Cell Biol., 2020, 98(4): 287-304.

Cupit, et al., Cloning and Expression of Single Chain Antibody Fragments in *Escherichia coli* and Pichia pastoris, Letters in Applied Microbiology, vol. 29, Issue 5, pp. 273-277, Nov. 1, 1999.

Dailey, et al., Sequences in the Polyomavirus DNA Regulatory Region Involved in Viral DNA Replication and Early Gene Expression, Journal of Virology, vol. 54, No. 3, pp. 739-749, Jun. 1, 1985.

Drapeau, et al., Extracellular Insulin Degrading Activity Creates Instability in a CHO-Based Batch-Refeed Continuous Process, Cytotechnology, vol. 15, Issue 1-3, pp. 103-109, Feb. 1, 1994.

Giudicelli et al., IMGT/LIGM-DB, the IMGT® comprehensive database of immunoglobulin and T cell receptor nucleotide sequences, Nucleic Acids Res., 2006, 34(suppl. 1): D781-D784.

Hoekema, et al., Codon Replacement in the PGK1 Gene of *Saccharomyces cerevisiae*: Experimental Approach to Study the Role of Biased Codon Usage in Gene Expression, Molecular and Cellular Biology, vol. 7, No. 8, pp. 2914-2924, Aug. 1, 1987.

Keen, et al., Development of a Serum-Free Culture Medium for the Large Scale Production of Recombinant Protein from a Chinese Hamster Ovary Cell Line, Cytotechnology, vol. 17, Issue 3, pp. 153-163, Oct. 1, 1995.

Mizushima, et al., pEF-BOS, A Powerful Mammalian Expression Vector, Nucleic Acids Research, vol. 18, No. 17, p. 5322, 1990.

Pear, et al., Production of High-Titer Helper-Free Retroviruses by Transient Transfection, Proceedings of the National Academy of Sciences of the United States of America, vol. 90, No. 18, pp. 8392-8396, 1993.

Sánchez, et al., High Cytoplasmic Expression in E. coli, Purification, and in vitro Refolding of a Single Chain Fv Antibody Fragment Against the Hepatitis B Surface Antigen, Journal of Biotechnology, vol. 72, Issues 1-2, pp. 13-20, 1999.

Scharfenberg, et al., A Reliable Strategy for the Achievement of Cell Lines Growing in Protein-Free Medium, Animal Cell Technology: Developments Towards the 21st Century, pp. 619-623, 1995.

Extended European Search Report for European Patent Application No. 22315214.1, mailed Jan. 26, 2023.

Tang et al., Impact of IgG subclass on molecular properties of monoclonal antibodies, MABS, Jan.-Dec. 2021, 13(1): 1993768, ePub Nov. 11, 2021.

Alam, J. and Cook, J.L., Reporter Genes: Application to the Study of Mammalian Gene Transcription. Anal Biochem. 1990; 188(2):245-54.

Ali, S. et al., IL-1 receptor Accessory Protein is Essential for IL-33-induced Activation of T Lymphocytes and Mast Cells. Proc Natl Acad Sci USA, 2007; 104(47):18660-5.

Balagurunathan, Y. et al., Gene Expression Profiling-Based Identification of Cell-Surface Targets for Developing Multimeric Ligands in Pancreatic Cancer. Mol Cancer Ther. 2008: 7(9):3071-80.

Barbas, C.F., III et al., In vitro Evolution of a Neutralizing Human Antibody to Human Immunodeficiency Virus Type 1 to Enhance Affinity and Broaden Strain Cross-Reactivity. Proc Natl Acad Sci USA. 1994; 91(9):3809-13.

Bardin, "Canakinumab for the Patient With Difficult-to-Treat Gouty Arthritis: Review of the Clinical Evidence", Joint Bone Spine, 2015, 82: eS9-eS16.

(56) References Cited

OTHER PUBLICATIONS

Barnes, L.M. et al., Advances in Animal Cell Recombinant Protein Production: GS-NSO Expression System. Cytotechnology. 2000; 32(2):109-23.

Barnes, L.M. et al., Characterization of the Stability of Recombinant Protein Production in the GS-NSO Expression System. Biotech Bioeng. 2001; 73(4):261-70.

Brueggemann, M. et al., Comparison of the Effector Functions of Human Immunoglobulins Using a Matched Set of Chimeric Antibodies. J Exp Med. 1987; 166(5):1351-61.

Capel, P.J.A. et al., Heterogeneity of Human IgG Fc Receptors. Immunomethods. 1994; 4(1):2534.

Carter, P. et al., Humanization of an Anti-p185HER2 Antibody for Human Cancer Therapy. Proc Natl Acad Sci USA. 1992; 89(10):4285-9.

Chin, J.W. and Schultz, P.G., In Vivo Photocrosslinking with Unnatural Amino Acid Mutagenesis. ChemBioChem. 2002; 3(11):1135-7.

Chin, J.W. et al., Addition of a Photocrosslinking Amino Acid to the Genetic Code of *Escherichia coli*. Proc Natl Acad Sci U.S.A. 2002; 99(17):11020-4.

Chin, J.W. et al., Addition of p-Azido-L-phenylalanine to the Genetic Code of *Escherichia coli*. J Amer Chem Soc. 2002; 124:9026-7.

Cullinan et al., The IL-1 Receptor Accessory Protein Is an Essential Component of the IL-1 Receptor, J. Immunology, Nov. 15, 1998, 161(10): 5614-5620.

Daeron, M., Fc Receptor Biology. Annu Rev Immunol. 1997; 15:203-34.

Davis, R.S. et al., Fc Receptor Homologs: Newest Members of a Remarkably Diverse Fc Receptor Gene Family. Immunol Rev. 2002; 190:123-36.

De Haas et al., Fcγ Receptors of Phagocytes. J Lab Clin Med. 1995; 126(4):330-41.

De Wet, J.R. et al., Firefly Luciferase Gene: Structure and Expression in Mammalian Cells. Mol Cell Biol. 1987; 7:725-37.

De Wildt, R.M. and Hoet, R.M., The Recovery of Immunoglobulin Sequences from Single Human B Cells by Clonal Expansion. Methods Mol Biol. 2002; 178:121-31.

Dinarello, C.A., Immunological and Inflammatory Functions of the Interleukin-1 Family, Annual Review of Immunology, 2009, 27: 519-550.

Dinarello, C.A., Interleukin-1 in the Pathogenesis and Treatment of Inflammatory Diseases. Blood. 2011; 117(14):3720-32.

Diu et al., Activation of resting human B cells by helper T-cell clone supernatant: characterization of a human B-cell-activating factor, PNAS USA, 1987, 84(24): 9140-9144.

Durocher, Y. et al., High-level and High-throughput Recombinant Protein Production by Transient Transfection of Suspension-growing Human 293-EBNA1 Cells. Nucleic Acids Res. 2002; 30(2):E9 (9 pages).

Edelman, et al., "The Covalent Structure of an Entire γG Immunoglobulin Molecule", PNAS USA, May 1, 1969, 63(1): 78-85.

Extended European Search Report for European Patent Application No. 21191122.7, mailed Nov. 24, 2021.

Geisse, S. et al., Eukaryotic Expression Systems: A Comparison. Protein Expr Purif. 1996; 8(3):271-82.

Guyer, R.L. et al., Immunoglobulin Binding by Mouse Intestinal Epithelial Cell Receptors. J Immunol. 1976; 117(2):587-93.

Hawkins, R.E. et al., Selection of Phage Antibodies by Binding Affinity: Mimicking Affinity Maturation. J Mol Biol. 1992; 226(3):889-96.

Hoffmann, P. et al., Murine Bone Marrow-derived Macrophages Constitute Feeder Cells for Human B Cell Hybridomas. J Immunol Methods. 1996; 196(1):85-91.

Huang, J. et al., Recruitment of IRAK to the Interleukin 1 Receptor Complex Requires Interleukin 1 Receptor Accessory Protein. Proc Natl Acad Sci USA. 1997; 94(24):12829-32.

Huston, J.S., Protein Engineering of Single-Chain Fv Analogs and Fusion Proteins. Methods Enzymol. 1991; 203:46-88.

International Preliminary Report on Patentability for PCT International Patent Application No. PCT/EP2016/064588, mailed Dec. 26, 2017.

International Search Report and Written Opinion for PCT International Patent Application No. PCT/EP2016/064588, mailed Jan. 11, 2017.

International Search Report and Written Opinion for PCT International Patent Application No. PCT/EP2017/060925, mailed Jul. 7, 2017.

International Search Report and Written Opinion for PCT International Patent Application No. PCT/EP2018/061846, mailed Jul. 6, 2018, 12 pages.

Jackson, J.R. et al., In vitro Antibody Maturation. Improvement of a High Affinity, Neutralizing Antibody Against IL-1 R. J Immunol. 1995; 154(7):3310-9.

Jaras, M. et al., Isolation and Killing of Candidate Chronic Myeloid Leukemia Stem Cells by Antibody Targeting of IL-1 Receptor Accessory Protein. Proc Natl Acad Sci USA. 2010; 107(37):16280-5.

Jefferis, R. et al., Interaction Sites on Human IgG-Fc for FOR: Current Models. Immunol Lett. 2002; 82(1-2):57-65.

Johnson, G. and Wu, T.T., Kabat Database and Its Applications: 30 Years After the First Variability Plot. Nucleic Acids Res. 2000; 28(1):214-8.

Kaufman, R.J., Overview of Vector Design for Mammalian Gene Expression. Mol Biotechnol. 2000; 16(2):151-60.

Kim, J.-K et al., Localization of the Site of Murine IgG1 Molecule that is Involved in Binding to the Murine Intestinal Fc Receptor. Eur J Immunol. 1994; 24(10):2429-34.

Kodituwakko, A.P. et al., Isolation of Antigen-Specific B Cells. Immunol Cell Biol. 2003; 81(3):163-70.

Krupke, D.M. et al., The Mouse Tumor Biology Database. Nat Rev Cancer. 2008; 8(6):459-65.

LeFranc, M.-P., Nomenclature of the Human Immunoglobulin Genes. Curr Protoc Immunol. 2000; Appendix 1P (37 pages).

Li, X. et al., Mutant Cells That Do Not Respond to Interleukin-1 (IL-1) Reveal a Novel Role for IL-1 Receptor-Associated Kinase. Mol Cel Biol. 1999; 19(7):4643-52.

Love, T.W. et al., Recombinant Antibodies Possessing Novel Effector Functions. Methods Enzymol. 1989; 178:515-27.

Makrides, S.C., Components of Vectors for Gene Transfer and Expression in Mammalian Cells. Protein Expr Purif. 1999; 17(2):183-202.

Mansur et al., Engagement of IL-1 receptor accessory protein (IL-1RAcP) with the monoclonal antibody AY19 provides co-activating signals and prolongs the CD2-induced proliferation of peripheral blood lymphocytes, Immunol Lett., 2011, 139(1):52-57.

Marks, J.D. et al., Bypassing Immunization: Building High Affinity Human Antibodies by Chain Shuffling. BioTechnology. 1992; 10(7):779-83.

Morrison, S.L. et al., Chimeric Human Antibody Molecules: Mouse Antigen-Binding Domains with Human Constant Region Domains. Proc Natl Acad Sci USA. 1984; 81(21):6851-5.

Neuberger, M.C. et al., A Hapten-Specific Chimaeric IgE with Human Physiological Effector Function. Nature. 1985; 314(6008):268-70.

Norderhaug, L. et al., Versatile Vectors for Transient and Stable Expression of Recombinant Antibody Molecules in Mammalian Cells. J Immunol Methods. 1997; 204(1):77-87.

Orencole, S.F. and Dinarello, C.A., Characterization of a Subclone (D10S) of the D10.G4.1 Helper T-cell Line which Proliferates to Attomolar Concentrations of Interleukin-1 in the Absence of Mitogens. Cytokine. 1989; 1(1):14-22.

Orlandi, R. et al., Cloning Immunoglobulin Variable Domains for Expression by the Polymerase Chain Reaction. Proc Natl Acad Sci USA. 1989; 86(10):3833-7.

Ow, D.W. et al., Transient and Stable Expression of the Firefly Luciferase Gene in Plant Cells and Transgenic Plants. Science. 1986; 234(4778):856-9.

Paul, William, Fundamental Immunology, 3rd Edition, Raven Press, New York, 1993, pp. 292-295.

(56) References Cited

OTHER PUBLICATIONS

Raju, T.S., Glycosylation Variations with Expression Systems and Their Impact on Biological Activity of Therapeutic Immunoglobulins. BioProcess Intl. 2003; 1(4):44-53.
Ravetch, J.V. and Kinet, J.P., Fc Receptors. Annu Rev Immunol. 1991; 9:457-92.
Riechmann, L. et al., Reshaping Human Antibodies for Therapy. Nature. 1988; 332:323-7.
Routier, F.H., The Glycosylation Pattern of a Humanized IgGI Antibody (D1.3) Expressed in CHO Cells. Glycoconj J. 1997; 14(2):201-7.
Roy, A. et al., Increased Efficiency of 7-Irradiated versus Mitomycin C-Treated Feeder Cells for the Expansion of Normal Human Cells in Long-Term Cultures. J Hematother Stem Cell Res. 2001; 10(6):873-80.
Rudikoff et al., Single amino acid substitution altering antigen-binding specificity, PNAS USA, Mar. 1982, 79: 1979-1983.
Schier, R. et al., Identification of Functional and Structural Amino-Acid Residues by Parsimonious Mutagenesis. Gene. 1995; 169(2):147-55.
Schlaeger, E.-J and Christensen, K., Transient Gene Expression in Mammalian Cells Grown in Serum-Free Suspension Culture. Cytotechnology. 1999; 30(1-3):71-83.
Schlaeger, E.-J., The Protein Hydrolysate, Primatone RL, is a Cost-Effective Multiple Growth Promoter of Mammalian Cell Culture in Serum-Containing and Serum-Free Media and Displays Anti-Apoptosis Properties. J Immunol Methods. 1996; 194(2):191-9.
Sonderman, P. et al., The 3.2-A Crystal Structure of the Human IgG1 Fc Fragment-FcγRIII Complex. Nature. 2000; 406(6793):267-73.
Towne, J.E. et al., Interleukin (IL)-1 F6, IL-1F8, and IL-F9 Signal Through IL-1 Rrp2 and IL-1RAcP to Activate the Pathway Leading to NF-KB and MAPKs. J Biol Chem. 2004; 279(14):13677-13688.
Umaña et al., Engineered Glycoforms of an Antineuro-Blastoma IgG1 with Optimized Antibody-Dependent Cellular Cytotoxic Activity. Nature Biotechnol. 1999; 17(2):176-80.
Vajdos et al., Comprehensive Functional Maps of the Antigen-Binding Site of an Anti-ErbB2 Antibody Obtained with Shotgun Scanning Mutagenesis, Journal of Molecular Biology, 2002, 320: 415-428.
Wang, L. and Schultz, P.G., Expanding the Genetic Code. Chem Commun. 2002; 0(1):1-11.
Wedemayer, G.J. et al., Structural Insights into the Evolution of an Antibody Combining Site. Science. 1997; 276(5319):1665-9.
Wen, L. et al., Limiting Dilution Assay for Human B Cells Based on Their Activation by Mutant EL4 Thymoma Cells: Total and Anti-Malaria Responder B Cell Frequencies. Eur J Immunol. 1987; 17(6):887-92.
Werner, R.G., Appropriate Mammalian Expression Systems for Biopharmaceuticals. Arzneimittelforschung. 1998; 48(8):870-80.
Windheim, M. et al., Interleukin-1 (IL-1) Induces the Lys63-linked Polyubiquitination of IL-1 Receptor-Associated Kinase 1 to Facilitate NEMO Binding and the Activation of 1-K13a Kinase. Mol Cell Biol. 2008; 28(5):1783-91.
Wood, K.V., Firefly Luciferase: A New Tool for Molecular Biologists. Promega Notes. 1990; 28:1-3.
Yamane-Ohnuki, N. and Satoh, M., Production of Therapeutic Antibodies with Controlled Fucosylation. MAbs. 2009; 1(3):230-6.
Yelton, D.E. et al., Affinity Maturation of the BR96 Anti-Carcinoma Antibody by Codon-Based Mutagenesis. J Immunol. 1995; 155(4):1994-2004.
Yoon, D.-Y. and Dinarello, C.A., Antibodies to Domains II and III of the IL-1 Receptor Accessory Protein Inhibit IL-1R Activity But Not Binding: Regulation of IL-1 Responses Is via Type I Receptor, Not the Accessory Protein. J Immunol. 1998; 160:3170-9.
Yoon, D.-Y. and Dinarello, C.A., Differential Effects of Anti-IL-1 R Accessory Protein Antibodies on IL-1a or IL-1 R-induced Production of PGE(2) and IL-6 from 3T3-L1 Cells. J Biochem Mol Biol. 2007; 40(4): 562-70.
Zhao et al., Construction of hydridoma calls with ILIRAP as a new marker for leukemia stem cells and detection of its monoclonal antibody, Journal of Exp Hematology, 2013, 21(6): 1390-1393.
Zubler, Polyclonal B Cell Responses in the Presence of Defined Filler Cells: Complementary Effects of Lipopolysaccharide and Anti-Immunoglobulin Antibodies, Eur J Immunol., 1984, 14(4):,357-363.
U.S. Appl. No. 15/739,410 2019/0106487 U.S. Pat. No. 10,906,971, filed Dec. 22, 2017 Apr. 11, 2019 Feb. 2, 2021, Stephan Fischer, Monoclonal Anti-IL-1RACP Antibodies.
U.S. Appl. No. 16/898,074 2020/0407438 U.S. Pat. No. 11,198,728, filed Jun. 10, 2020 Dec. 31, 2020 Dec. 14, 2021, Stephan Fischer, Monoclonal Anti-IL-1RACP Antibodies.
U.S. Appl. No. 17/522,600 2022/0169718, filed Nov. 9, 2021 Jun. 2, 2022, Stephan Fischer, Monoclonal Anti-IL-1RACP Antibodies.
U.S. Appl. No. 16/099,059 2019/0194336 U.S. Pat. No. 11,203,642, filed Nov. 5, 2018 Jun. 27, 2019 Dec. 21, 2021, Stephan Fischer, Humanized Anti-IL-1R3 Antibodies.
U.S. Appl. No. 17/410,153 2022/0089751, filed Aug. 24, 2021 Mar. 24, 2022, Stephan Fischer, Humanized Anti-IL-1R3 Antibodies.
U.S. Appl. No. 16/612,052 2020/0140559 U.S. Pat. No. 11,639,392, filed Nov. 8, 2019 May 7, 2020 May 2, 2023, Stephan Fischer, Anti-IL-1R3 Antibodies for Use in Inflammatory Conditions.
U.S. Appl. No. 18/184,759, filed Mar. 16, 2023, Stephan Fischer, Anti-IL-1R3 Antibodies for Use in Inflammatory Conditions.
U.S. Appl. No. 18/471,388, filed Sep. 21, 1023, Christian Lange, Humanized Anti-IL-1R3 Antibody and Methods of Use.

* cited by examiner

HUMANIZED ANTI-IL-1R3 ANTIBODY AND METHODS OF USE

RELATED APPLICATIONS

This application claims priority to European Patent Application No. 22315214.1, filed Sep. 21, 2022, the entire disclosure of which is hereby incorporated herein by reference in its entirety.

SEQUENCE LISTING

The instant application contains a Sequence Listing which has been submitted electronically in XML format and is hereby incorporated by reference in its entirety. Said XML file, created on Sep. 18, 2023, is named 745480_SA9-339_ST26.xml and is 53,349 bytes in size.

FIELD

An antibody that specifically binds to IL-1R3 and comprises an antibody heavy chain amino acid sequence of SEQ ID NO: 1 and a light chain amino acid sequence of SEQ ID NO: 2. Also a method for treating a disease or disorder in a subject in need thereof comprising administering to the subject said antibody.

BACKGROUND

Interleukin-1 (IL-1) is a central mediator of innate immunity and inflammation. The type 1 IL-1 receptor (IL-1R1) and the IL-1 receptor accessory protein (IL-1RAcP, also known as IL-1R3) form a functional IL-1 receptor complex that is thought to mediate most, if not all, IL-1-induced effects. In addition to IL-1R1, IL-1R3 is also serves as a receptor subunit for the heterodimeric IL-33 and IL-36 receptor complexes. Thus, IL-1R3 plays a role in three signaling pathways that involve six cytokines of the IL-1 family (IL-1α, IL-1β, IL-33, IL-36α, IL-36β and IL-36γ). IL-1 family cytokines are potent mediators of inflammation, acting to coordinate local and systemic immune responses to a wide range of stimuli. Aberrant signaling by IL-1 family cytokine members, however, is linked to myriad inflammatory syndromes, autoimmune conditions and cancers. A tight regulation of IL-1 family cytokine signaling pathways via receptor antagonists, decoy receptors, and signaling inhibitors ensures a balance between amplification of innate immunity and uncontrolled inflammation. There is human genetic validation linking the IL-1 family signaling pathways to autoimmune diseases. As inhibition of IL-1R3 can inhibit all three signaling pathways, blocking IL-1R3 is a multi-targeting strategy that would neutralize three cytokine pathways (IL-1, IL-33 and IL-36) and confer efficacy in indications where single cytokine targeting may not be sufficient. Thus, there is a need for the development of therapeutic anti-IL-1R3 antibodies. For several years, attempts have been made to generate functional monoclonal antibodies (mAbs) against human IL-1R3. However, there is need for improved anti-IL-1R3 antibodies. In particular, there is a need for anti-IL-1R3 antibodies having advantages in terms of excellent inhibition of the three signaling pathways without implications on other cellular pathways.

SUMMARY

In a first aspect, an antibody is provided that specifically binds to IL-1R3, comprising an antibody heavy chain amino acid sequence of SEQ ID NO: 1 and a light chain amino acid sequence of SEQ ID NO: 2.

In a second aspect, a pharmaceutical composition is provided comprising the antibody of the first aspect and a pharmaceutically acceptable diluent, carrier or excipient.

In a third aspect, provided is an isolated nucleic acid molecule is provided encoding the antibody of the first aspect.

In a fourth aspect, an expression vector is provided comprising the nucleic acid molecule of the third aspect.

In a fifth aspect, a host cell is provided comprising the expression vector of the fourth aspect.

A sixth aspect relates to a method of manufacturing the antibody of the first aspect comprising the steps of: (i) optionally transfecting a host cell using the isolated nucleic acid molecule of third aspect or the expression vector of the fourth aspect; (ii) cultivating the host cell under conditions allowing expression of the antibody; (iii) recovering the antibody; and (iv) optionally further purifying and/or modifying and/or formulating the antibody.

A seventh aspect relates to an antibody produced by the method of manufacturing according to the sixth aspect.

An eighth aspect relates to the antibody of the first aspect for use in treating a disease or disorder in a subject in need thereof, preferably wherein the disease or disorder is an autoimmune or autoinflammatory disease or disorder.

A ninth aspect relates to the pharmaceutical composition of the second aspect for use in treating a disease or disorder in a subject in need thereof, preferably wherein the disease or disorder is an autoimmune or autoinflammatory disease or disorder.

In a tenth aspect, provided is a method for treating a disease or disorder in a subject in need thereof comprising administering to the subject the antibody of the first aspect or the pharmaceutical composition of the second aspect.

BRIEF DESCRIPTION OF THE FIGURES

The foregoing and other features and advantages of the present disclosure will be more fully understood from the following detailed description of illustrative embodiments taken in conjunction with the accompanying drawings.

DETAILED DESCRIPTION

Figure 1:
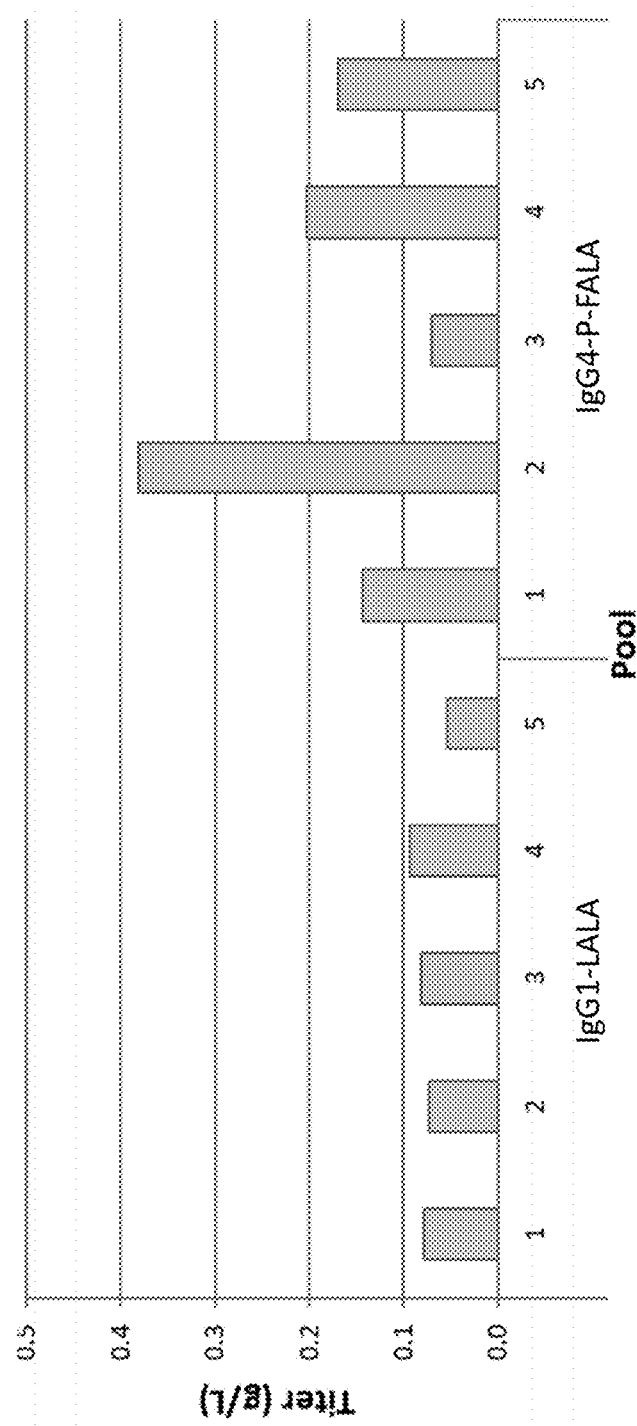
FIG. 1 depicts the anti-IL-1R3 antibody titer of 50 nM methotrexate (MTX) selected pools after transfection. The pools express anti-IL-1R3 antibodies comprising an Fc region of either IgG1 with L234A and L235A mutations (IgG1-LALA) or IgG4 with S228P, F234A, and L2345A mutations (IgG4-P-FALA).

Human immunoglobulin G isotype 4 (IgG4) antibodies (Abs) are potential candidates for immunotherapy when reduced effector functions are desirable.

Certain mutations in the Fc region of IgG4 Ab may further reduce effector functions. IgG4 residues 234 and 235 according to EU index (Proc Natl Acad Sci US A. 1969, 63 (1), 78-85; Kabat et al., Sequences of proteins of immunological interest, 1991 Fifth edition) can be mutated such that phenylalanine at position 234 is changed to alanine (F234A) and leucine at position 235 is changed to alanine (L235A) (Parekh et al. 2012—see Literature Cited section). Such antibody mutations are called FALA mutations. However, IgG4 Abs are dynamic molecules able to undergo Fab arm exchange (FAE) resulting in functionally monovalent, bispecific antibodies (bsAbs) with potentially reduced therapeutic efficacy. The amino acid residues serine at position 228 (S228) and arginine at position 409 of IgG4 drive the FAE (Labrijn et al., 2011—see Literature Cited section). Substitution of the S228 with proline (S228P) was shown to prevent IgG4 FAE and thus stabilize IgG4 Abs (Angal et al., 1993; Silva et al., 2015—see Literature Cited section). The above-mentioned FALA mutation and S228P mutation may be introduced simultaneously into the constant region of the antibody. An IgG4 heavy chain having a FALA mutation is referred to as an "IgG4 FALA" type heavy chain, an IgG4 heavy chain having the S228P mutation is referred to as an "IgG4-P" type heavy chain, and an IgG4 heavy chain having both a FALA mutation and a S228P mutation is referred to as "IgG4-P-FALA" Ab.

WO2017191325A1 (Fischer et al., MAB Discovery GmbH) relates to a humanized antibody that specifically binds to IL-1R3 or a fragment or derivative thereof and specifically describes substitutions at L234A and L235A of the human IgG1 Fc region (an "IgG1-LALA" format) or S228P and L235E of the human lgG4 Fc region (an "IgG4-PE" format).

As outlined in the Background section herein, it is exceedingly difficult to identify mAb with high affinity, high specificity, and potent neutralizing activity against IL-1R3. Surprisingly, the inventors have developed such an antibody and this antibody has further advantages. The present disclosure encompasses a humanized IL-1R3 antibody, with high affinity and specificity for IL-1R3, with potent IL-1R3 neutralizing activity, reduced effector functions, and improved stability. The antibody disclosed herein shows reduced or no Fcγ-receptor signaling and does not induce antibody dependent cell-mediated cytotoxicity (ADCC). Surprisingly, the antibody disclosed herein has significantly higher production yield in IgG4-P-FALA format as compared to the more common IgG1-LALA format.

In order for the antibody as disclosed herein to be industrially useful, it needs to be able to be incorporated into a composition having certain favourable characteristics. For example, the composition should be stable over time in that preservatives can be used without effect on the antibody. The viscosity and opalescence of the composition should remain within specific parameters and not change over time e.g., during storage. The antibody's 3D structure is critical for its function and binding to its target. Hence, it should not aggregate (self-associate) or minimally aggregate in the composition and other excipients in the composition should not induce changes in the antibody's 3D structure or increase self-association. Particularly important are the isoelectric point and self-association values, both done with the antibody in a standard dilute composition as well as the opalescence value in a concentrated composition. A benchmark tolerance window needs to be met for various parameters in order for the antibody to be able to be formulated for use on a commercial scale.

In general, a higher isoelectric point correlates with higher antibody stability, a lower kD value for self-association correlates with higher affinity and thus a higher likelihood for self-association, and a higher turbidity value (NTU) is less desirable as clear solutions are important. As can be understood for the median values for a series of different antibodies in either IgG1 or IgG4 Fc formats (see Table 1 below), the latter format tends to result in less desired values for the formulatability parameters. Surprisingly, the anti-IL-1R3-IgG4-P-FALA Ab disclosed herein met the benchmark window in that the value was sufficiently close to the median value to be viable on a commercial scale.

TABLE 1

Median values for various parameters for antibodies with IgG1 Fc or IgG4 Fc format.

|  | Median value for a series of different antibodies having an IgG1 Fc | Median value for a series of different antibodies having an IgG4 Fc | Anti-IL-1R3-IgG4-P-FALA |
| --- | --- | --- | --- |
| Isoelectric point (pI) | 8.2 | 6.5 | Meets benchmark window |
| Self-association (kD in mL/g) | 36 | −10 | Meets benchmark window |
| Opalescence (NTU) | 6 | 21 | Meets benchmark window |

It is notable that several anti-IL-1R3 antibodies and other IL-1/IL-33/IL-36 receptor superfamily-targeting antibodies in the art do not employ the IgG4-P-FALA Fc of the disclosure. Rather, many of these antibodies employ the IgG1-LALA Fc. For example, the antibody CAN04 (described in U.S. Pat. No. 9,796,783, Ågerstam et al.), the antibody CAN10 (described in WO2022/136569 A1, Liberg et al.), and spesolimab (anti-IL-36R, described in Chenoweth et al. Immunol Cell Biol. 2020. 98(4): 287-304) all employ the IgG1-LALA Fc. The same applies to the anti-IL-1R3 antibodies disclosed in WO2022/053715 A1 (Macoin et al.), WO2022/170008 A2 (Bigwarfe et al.) and WO2022/243536 A1 (Urso et al.), which all employ the IgG1-LALA Fc. The inventors surprisingly found that the antibody of the invention has a substantially higher production yield as compared to the IgG1-LALA format commonly used for anti-IL-1R3 antibodies.

The present disclosure describes an anti-IL-1R3 antibody comprising at least amino acid substitutions S228P, F234A and L235A of the human IgG4 Fc region. In particular, the present disclosure relates to an antibody that specifically binds to IL-1R3 and shows reduced or no FCγ-receptor signaling and comprises antibody heavy chain amino acid sequence of SEQ ID NO: 1 and a light chain amino acid sequence of SEQ ID NO: 2.

The aspects of the present disclosure are hereinafter described in more detail.

I. Definitions and Antibodies of the First Aspect

Unless otherwise stated, all technical and scientific terms used in the present disclosure have the same meanings as commonly understood by one of ordinary skill in the art to which this disclosure belongs. Any methods and materials similar or equivalent to those described herein can be used in the methods of techniques of the present disclosure. All publications cited herein are incorporated herein by reference in their entirety for the purpose of describing and disclosing the methodologies, reagents, and tools reported in the publications that might be used in connection with the disclosure.

The methods and techniques of the present application are generally performed according to conventional methods well known in the art and as described in various general and more specific references that are cited and discussed throughout the present specification unless otherwise indicated. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M. and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R. and Graham, A., eds. (1997) PCR (Introduction to Biotechniques Series), 2nd ed., Springer-Verlag.

The term "antibody," unless indicated otherwise, is used to refer to entire antibodies as well as antigen-binding fragments of such antibodies. For example, the term encompasses four-chain IgG molecules, as well as antibody fragments.

As used herein, the term "antibody fragment" refers to portions of an intact full-length antibody, for example, as further described below.

Naturally occurring immunoglobulins have a common core structure in which two identical light chains (about 24 kDa) and two identical heavy chains (about 55 or 70 kDa) form a tetramer. The amino-terminal portion of each chain is known as the variable (V) region and can be distinguished from the more conserved constant (C) regions of the remainder of each chain.

Most of the amino acid sequence variation in immunoglobulins is confined to three separate locations in each of the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3 and FR4, respectively. Proceeding from the amino-terminus, these combined regions comprised in a V region are designated FR1, CDR1, FR2, CDR2, FR3, CDR3, and FR4. The locations of CDR and FR regions and a numbering system have been defined by Kabat et al. (Kabat, E. A. et al., Sequences of Proteins of Immunological Interest, Fifth Edition, U.S. Department of Health and Human Services, U.S. Government Printing Office (1991), and updates thereof which may be found online). In addition, CDR region boundaries have been further defined by IMGT nomenclature.

A "humanized mAb," as used herein, is an antibody which is composed of a human antibody framework, into which have been grafted complementarity determining regions (CDRs) from a non-human antibody. Changes in the human acceptor framework may also be made. Procedures for the design and production of humanized antibodies are well known in the art, and have been described, for example, in U.S. Pat. No. 4,816,397 (Boss et al.); U.S. Pat. No. 4,816,567 (Cabilly et al.); U.S. Pat. No. 5,225,539 (Winter, MRC); EP0120694A2 (Boss et al.); EP0125023A1 (Cabilly et al.); EP0194276B1 (Neuberger & Rabbitts); EP0239400A2 (Winter, MRC); EP0519596A1 (Padlan et al.); and WO1986001533 (Neuberger & Rabbitts). Further details on antibodies, humanized antibodies, human engineered antibodies, and methods for their preparation can be found in Kontermann, R. and Dijbel, S. eds. (2001, 2010) Antibody Engineering, 2nd ed., Springer-Verlag, New York, NY. The entire contents of each of the patents and patent application publications listed above are incorporated herein by reference.

Constant regions may be derived from any human antibody constant regions. Variable region genes may be cloned into expression vectors in frame with constant region genes to express heavy and light immunoglobulin chains. Such expression vectors can be transfected into antibody producing host cells for antibody synthesis.

Human antibody variable and constant regions may be derived from sequence databases. For example, immunoglobulin sequences are available in the IMGT/LIGM database (Giudicelli et al., [2006] Nucleic Acids Res. 34 [suppl. 1]: D781-D784) or VBase 30 (vbase.mrc-cpe.cam.ac.uk). Aglycosylated antibodies can have extensively modified functionality; see, Boyd et al. (1996) Mol. Immunol. 32:1311-1318. A "delta ab" or Δab modification, as used herein, is an Fc modification as described in Armour et al., (1999) Eur. J. Immunol. 29:2613-2624.

The terms "stable", "stability", and "stabilized", as used herein in the context of a binding polypeptide, refer to the resistance of the binding polypeptide to thermal and chemical degradation or fragmentation under given conditions of manufacture, preparation, transportation and storage. The "stable" compositions retain biological activity greater than or equal to 80%, 85%, 90%, 95%, 98%, 99%, 99.5%, or 99.9% under given manufacture, preparation, transportation and storage conditions. The stability of a binding polypeptide can be assessed, for example, in terms degrees of degradation or fragmentation, or levels of particular fragments or types or sizes of aggregates, compared to a control or compared to a starting material, using methods and measurements known to those skilled in the art. Such methods and measurements include, but are not limited to, reduced area under the curve (AUC), size exclusion chromatography (SEC), high performance (or high pressure) size exclusion chromatography (HPSEC), liquid chromatography-mass spectrometry (LC-MS), capillary gel electrophoresis (CGE), and sodium dodecyl sulfate polyacrylamide gel electrophoresis (SDS-PAGE), compared to a reference.

The term "nucleic acid," as used herein, includes DNA molecules which encode the antibodies described herein. Preferred DNA molecules which encode the antibodies described herein are expression vectors, which are suitable for expressing the antibody genes in a host cell. Expression vectors and host cells for antibody gene expression are known in the art; see, for example, Morrow, K. J. Genetic Engineering & Biotechnology News (Jun. 15, 2008) 28(12), and Backliwal, G. et al. (2008) Nucleic Acids Res. 36(15): e96-e96.

The terms "treat" and "treatment," as used herein, refer to the care of a patient or subject having a disease, disorder, or condition. The treatment may be directed to, but is not limited to, any one or any combination of the following: the cure of a disease, disorder, or condition; the improvement of at least one symptom of a disease, disorder, or condition; and/or a prophylactic or preventative act in which the aim is to prevent or reduce the occurrence of a disease, disorder, or condition. In certain embodiments, the treatment may be directed to, but is not limited to, the cure of a disease, disorder, or condition; or the improvement of at least one symptom of a disease, disorder, or condition.

The term "subject," as used herein, refers to any mammal, including mice, rats, gerbils, hamsters, guinea pigs, rabbits, cats, dogs, sheep, goats, pigs, cows, horses, and primates. In certain embodiments, a subject is a mammal other than a human. In certain embodiments, a subject is a non-human primate. In certain embodiments, a subject is a human.

The first aspect relates to an antibody that specifically binds to IL-1R3, comprising an antibody heavy chain amino acid sequence of SEQ ID NO: 1 and a light chain amino acid sequence of SEQ ID NO: 2.

In at least one embodiment, the antibody is a humanized mAb. In at least one embodiment, the antibody is an anti-IL-1R3 antibody.

A humanized mAb, or a humanized mAb fragment (e.g., an anti-IL-1R3 antibody or fragment thereof) may comprise an antibody constant region (e.g., a human IgG4 constant region) which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, IgG4 antibodies bind to receptors on various cells via the Fc region, with a Fc receptor binding site on the antibody Fc region binding to a Fc receptor (FcR) on a cell. Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer, and control of immunoglobulin production.

In certain embodiments, a humanized mAb, or a humanized mAb fragment (e.g., an anti-IL-1R3 antibody or fragment thereof) may comprise a constant region which is incapable of directing one or more effector functions (e.g., ADCC activity) and/or is unable to bind Fcγ (Fc gamma) receptor.

Certain embodiments described herein provide a humanized mAb, or a humanized mAb fragment (e.g., an anti-IL-1R3 antibody or fragment thereof) in which at least one amino acid in one or more of the constant region domains has been deleted or otherwise altered so as to provide desired biochemical characteristics such as, reduced effector functions.

In certain other embodiments, a humanized mAb, or a humanized mAb fragment (e.g., an anti-IL-1R3 antibody or fragment thereof) comprises an Fc region or portion thereof from a human IgG4 molecule and a Ser228Pro (S228P) mutation (EU numbering) in the core hinge region of the molecule.

In certain exemplary embodiments, the Fc portion of a humanized mAb, or a humanized mAb fragment (e.g., an anti-IL-1R3 antibody or fragment thereof) may be mutated to increase or decrease effector function using techniques known in the art. For example, the deletion or inactivation (through point mutations or other means) of a constant region domain may reduce Fc receptor binding of the circulating modified antibody. In other cases, it may be that constant region modifications consistent with the instant disclosure moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, bio-distribution and serum half-life, may easily be measured and quantified using well know immunological techniques without undue experimentation.

In certain embodiments, an Fc domain employed in a humanized mAb, or a humanized mAb fragment (e.g., an anti-IL-1R3 antibody or fragment thereof) is an Fc variant. As used herein, the term "Fc variant" refers to an Fc domain having at least one amino acid substitution relative to the wild-type Fc domain from which said Fc domain is derived. The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In addition to the P-FALA Fc mutations, the antibodies described herein may employ any other art-recognized Fc variant which is known to impart an improvement (e.g., reduction) in effector function and/or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein.

In certain embodiments, a humanized mAb, or a humanized mAb fragment (e.g., an anti-IL-1R3 antibody or fragment thereof) may comprise an Fc variant comprising an amino acid substitution which alters the antigen-independent effector functions of the antibody, in particular the circulating half-life of the antibody. Such antibodies exhibit either increased or decreased binding to neonatal Fc receptor (FcRn) when compared to antibodies lacking these substitutions, and therefore have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g., for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired.

In the first aspect, an antibody is provided that specifically binds to IL-1R3 and comprises an antibody heavy chain amino acid sequence of SEQ ID NO: 1 and a light chain amino acid sequence of SEQ ID NO: 2.

In an alternative embodiment, an antibody is provided that specifically binds to IL-1R3 and comprises an antibody heavy chain variable (VH) domain amino acid sequence of SEQ ID NO: 3, an antibody light chain variable (VL) domain amino acid sequence of SEQ ID NO: 4, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain, an antibody light chain variable (VL) domain, and an IgG4 Fc domain, wherein:
the VH domain comprises
a CDR-H1 sequence comprising the amino acid sequence of SYDMS (SEQ ID NO: 5) or GFSLSSYD (SEQ ID NO: 6);
a CDR-H2 sequence comprising the amino acid sequence of TIYIGGTTAYASWPKG (SEQ ID NO: 7) or IYIGGTT (SEQ ID NO: 8); and
a CDR-H3 sequence comprising the amino acid sequence of LQGANYYNSLAL (SEQ ID NO: 9) or ARLQG-ANYYNSLAL (SEQ ID NO: 10);
the VL domain comprises
a CDR-L1 sequence comprising the amino acid sequence of QASQSIYSFLS (SEQ ID NO: 11) or QSIYSF (SEQ ID NO: 12);
a CDR-L2 sequence comprising the amino acid sequence of ASDLES (SEQ ID NO: 13) or AAS (SEQ ID NO: 14); and
a CDR-L3 sequence comprising the amino acid sequence of QSNYIIDYGA (SEQ ID NO: 15 or SEQ ID NO: 16); and the IgG4 Fc domain comprises an F234A substitution and an L235A substitution, according to EU numbering.

In an alternative embodiment, an antibody is provided that specifically binds to IL-1R3 and comprises an antibody heavy chain variable (VH) domain, an antibody light chain variable (VL) domain, and an IgG4 Fc domain, wherein:
the VH domain comprises
a CDR-H1 sequence comprising the amino acid sequence of SYDMS (SEQ ID NO: 5) or GFSLSSYD (SEQ ID NO: 6);
a CDR-H2 sequence comprising the amino acid sequence of TIYIGGTTAYASWPKG (SEQ ID NO: 7) or IYIGGTT (SEQ ID NO: 8); and
a CDR-H3 sequence comprising the amino acid sequence of LQGANYYNSLAL (SEQ ID NO: 9) or ARLQG-ANYYNSLAL (SEQ ID NO: 10);
the VL domain comprises
a CDR-L1 sequence comprising the amino acid sequence of QASQSIYSFLS (SEQ ID NO: 11) or QSIYSF (SEQ ID NO: 12);
a CDR-L2 sequence comprising the amino acid sequence of ASDLES (SEQ ID NO: 13) or AAS (SEQ ID NO: 14); and
a CDR-L3 sequence comprising the amino acid sequence of QSNYIIDYGA (SEQ ID NO: 15 or SEQ ID NO: 16); and the IgG4 Fc domain comprises an F234A substitution, an L235A substitution, and an S228P substitution, according to EU numbering.

TABLE 2

Amino acid sequences of VH, VL and CDR regions of the exemplary anti-IL-1R3 IgG4-P-FALA antibody.

| Antibody | Sequence | SEQ ID NO: |
|---|---|---|
| Anti-IL-1R3-IgG4-P-FALA Heavy chain | EVQLEESGGRLVQPGTSLRLSCAVSGFSLSSYDMSW VRQAPGKGLEWVSTIYIGGTTAYASWPKGRFTISKT NSKNTLYLQMNSLRAEDTAVYFCARLQGANYYNSL ALWGQGTLVTVSSASTKGPSVFPLAPCSRSTSESTA ALGCLVKDYFPEPVTVSWNSGALTSGVHTFPAVLQS SGLYSLSSVVTVPSSSLGTKTYTCNVDHKPSNTKVD KRVESKYGPPCPPCPAPEAAGGPSVFLFPPKPKDTL MISRTPEVTCVVVDVSQEDPEVQFNWYVDGVEVHN AKTKPREEQFNSTYRVVSVLTVLHQDWLNGKEYKC KVSNKGLPSSIEKTISKAKGQPREPQVYTLPPSQEEM TKNQVSLTCLVKGFYPSDIAVEWESNGQPENNYKTT PPVLDSDGSFFLYSRLTVDKSRWQEGNVFSCSVMHE ALHNHYTQKSLSLSLG | 1 |

TABLE 2-continued

Amino acid sequences of VH, VL and CDR regions
of the exemplary anti-IL-1R3 IgG4-P-FALA antibody.

| Antibody | Sequence | SEQ ID NO: |
|---|---|---|
| Anti-IL-1R3-IgG4-P-FALA Light chain | DVQMTQSPSSLSASVGDRVTITCQASQSIYSFLSWY QQKPGQAPKLLIYAASDLESGVPSRFSGSGSGTDFTL TISSLQPEDFATYYCQSNYIIDYGAFGQGTKVVIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC | 2 |
| Anti-IL-1R3-IgG4-P-FALA VH domain | EVQLEESGGRLVQPGTSLRLSCAVSGFSLSSYDMSW VRQAPGKGLEWVSTIYIGGTTAYASWPKGRFTISKT NSKNTLYLQMNSLRAEDTAVYFCARLQGANYYNSL ALWGQGTLVTVSS | 3 |
| Anti-IL-1R3-IgG4-P-FALA VL domain | DVQMTQSPSSLSASVGDRVTITCQASQSIYSFLSWY QQKPGQAPKLLIYAASDLESGVPSRFSGSGSGTDFTL TISSLQPEDFATYYCQSNYIIDYGAFGQGTKVVIK | 4 |
| Anti-IL-1R3-IgG4-P-FALA CDR-H1 (Kabat numbering) | SYDMS | 5 |
| Anti-IL-1R3-IgG4-P-FALA CDR-H1 (IMGT numbering) | GFSLSSYD | 6 |
| ANTI-IL-1R3-IgG4-P-FALA CDR-H2 (Kabat numbering) | TIYIGGTTAYASWPKG | 7 |
| ANTI-IL-1R3-IgG4-P-FALA CDR-H2 (IMGT numbering) | IYIGGTT | 8 |
| ANTI-IL-1R3-IgG4-P-FALA CDR-H3 (Kabat numbering) | LQGANYYNSLAL | 9 |
| ANTI-IL-1R3-IgG4-P-FALA CDR-H3 (IMGT numbering) | ARLQGANYYNSLAL | 10 |
| ANTI-IL-1R3-IgG4-P-FALA CDR-L1 (Kabat numbering) | QASQSIYSFLS | 11 |
| ANTI-IL-1R3-IgG4-P-FALA CDR-L1 (IMGT numbering) | QSIYSF | 12 |
| ANTI-IL-1R3-IgG4-P-FALA CDR-L2 (Kabat numbering) | AASDLES | 13 |
| ANTI-IL-1R3-IgG4-P-FALA CDR-L2 (IMGT numbering) | AAS | 14 |
| ANTI-IL-1R3-IgG4-P-FALA CDR-L3 (Kabat numbering) | QSNYIIDYGA | 15 |
| ANTI-IL-1R3-IgG4-P-FALA CDR-L3 (IMGT numbering) | QSNYIIDYGA | 16 |

TABLE 2-continued

Amino acid sequences of VH, VL and CDR regions of the exemplary anti-IL-1R3 IgG4-P-FALA antibody.

| Antibody | Sequence | SEQ ID NO: |
|---|---|---|
| IgG4-P-FALA Fc domain | ESKYGPPCPPPCPAPEAAGGPSVFLFPPKPKDTLMISR TPEVTCVVVDVSQEDPEVQFNWYVDGVEVHNAKT KPREEQFNSTYRVVSVLTVLHQDWLNGKEYKCKVS NKGLPSSIEKTISKAKGQPREPQVYTLPPSQEEMTKN QVSLTCLVKGFYPSDIAVEWESNGQPENNYKTTPPV LDSDGSFFLYSRLTVDKSRWQEGNVFSCSVMHEAL HNHYTQKSLSLSLG | 17 |
| Human IgG1-Fc domain | EPKSCDKTHTCPPCPAPELLGGPSVFLFPPKP KDTLMISRTPEVTCVVVDVSHEDPEVKFNW YVDGVEVHNAKTKPREEQYNSTYRVVSVLT VLHQDWLNGKEYKCKVSNKALPAPIEKTIS KAKGQPREPQVYTLPPSRDELTKNQVSLTC LVKGFYPSDIAVEWESNGQPENNYKTTPPV LDSDGSFFLYSKLTVDKSRWQQGNVFSCSV MHEALHNHYTQKSLSLSPGK | 18 |

TABLE 3

Amino acid sequences of VH and VL regions of additional exemplary anti-IL-1R3 antibodies that may be employed in an IgG4-P-FALA Fc.

| Antibody | Sequence | SEQ ID NO: |
|---|---|---|
| CAN04 VH1 | QVQLQQSGPELLKPGASVKISCKASGYAFSSSWMN WVKQRPGKGLEWIGRIYPGDGNTHYSGKFKGKATL TADKSSSIAYMQLSSLTSEDSAVYFCGEGYLDPMDY WGQGTSVTVSS | 24 |
| CAN04 VH2 | QVQLVQSGAEVKKPGSSVKVSCKASGYAFSSSWMN WVRQAPGQGLEWMGRIYPGDGNTHYAQKFQGRVT LTADKSTSTAYMELSSLRSEDTAVYYCGEGYLDPM DYWGQGTLVTVSS | 25 |
| CAN04 VH3 | QVQLVQSGAEVKKPGSSVKVSCKASGYAFTSSWMN WVRQAPGQGLEWMGRIYPGDGNTHYAQKFQGRVT LTADKSTSTAYMELSSLRSEDTAVYYCGEGYLDPM DYWGQGTLVTVSS | 26 |
| CAN04 VH4 | QVQLVQSGAEVKKPGSSVKVSCKASGYTFTSSWMN WVRQAPGKGLEWMGRIYPGDGQTHYAQKFQGRVT LTADKSTSTAYMELSSLRSEDTAVYYCGEGYLDPM DYWGQGTLVTVSS | 27 |
| CAN04 VH5 | QVQLVQSGAEVKKPGSSVKVSCKASGYTFTSSWMN WVRQAPGKGLEWMGRIYPGDGQTHYAQKFQGRVT ITADKSTSTAYMELSSLRSEDTAVYYCGEGYLDPMD YWGQGTLVTVSS | 28 |
| CAN04 VL1 | DIQMTQTTSSLSASLGDRVTISCSASQGINNYLNWY QQKPDGTVKLLIHYTSGLHAGVPSRFSGSGSGTDYS LTISNLEPEDVATYYCQQYSILPWTFGGGTKLEIKR | 29 |
| CAN04 VL2 | DIQMTQSPSSLSASVGDRVTITCSASQGINNYLNWY QQKPGKAPKLLIHYTSGLHAGVPSRFSGSGSGTDYT LTISSLQPEDVATYYCQQYSILPWTFGGGTKVEIKR | 30 |
| CAN04 VL3 | DIQMTQSPSSLSASVGDRVTITCQASQGINNYLNWY QQKPGKAPKLLIHYTSGLHAGVPSRFSGSGSGTDYT LTISSLEPEDVATYYCQQYSILPWTFGGGTKVEIKR | 31 |
| CAN04 VL4 | DIQMTQSPSSLSASVGDRVTITCQASQGINNYLNWY QQKPGKAPKLLIHYTSGLHAGVPSRFSGSGSGTDFT LTISSLEPEDVATYYCQQYSILPWTFGGGTKVEIKR | 32 |
| CAN10 VH | QEQLEESGGGLVKPGGTLSLTCTVSGPSLSHFDITWI RQPPGKGLEWIGTISPGVSTYYASWAKSRVTISVDTS LNTVSLKLSSVTAADTATYFCARGGVGSSWKAFDL WGPGTLVTISS | 33 |

TABLE 3-continued

Amino acid sequences of VH and VL regions of additional exemplary anti-IL-1R3 antibodies that may be employed in an IgG4-P-FALA Fc.

| Antibody | Sequence | SEQ ID NO: |
| --- | --- | --- |
| CAN10 VL | ELVMTQSPSSVSASVGDRVTITCQASESISTALAWY QQKPGKAPKLLIYKASTLPSGVPSRFSGSGSGTDFTL TINSLQPEDFATYYCQQGFSSGNVHNAFGGGTKVEI K | 34 |
| ISB 880 VH | QVQLVQSGAEVKKPGSSVKVSCKASGSPAEPYAIQ WVRQAPGQGLEWMGYIIPSLGGYDYAQKFQGRVTI TADESTSTAYMELSSLRSEDTAVYYCARGQTLYESG RQFDIWGQGTLVTVSS | 35 |
| ISB 880 VL | EIVMTQSPATLSVSPGERATLSCRASQSVSSNLAWY QQKPGQAPRLLIYGASTRATGIPARFSGSGSGTEFTL TISSLQSEDFAVYYCQQYNNWPWTFGQGTKVEIK | 36 |
| GO11-A1 VH | QVHLQQSGPELVRPGTSVKISCEASGYIFLTYWMNW VKQRPGQGLEWIGQIFPASDSTYYNEMFKDKARFTV DKSSSTAYMQFSSLTSEDTAVYFCARSGPYSYYAGG YALDYWGQGTSVTVSS | 37 |
| GO11-A2 VH | QVQLVQSGAEVKKPGSSVKVSCKASGYIFLTYWMN WVRQAPGQGLEWMGQIFPASGSAYYNQKFKGRVTI TADKSTSTAYMELSSLRSEDTAVYYCARSGPYSYYA GGYALDYWGQGTLVTVSS | 38 |
| GO11-A3 VH | QVQLVQSGAEVKKPGSSVKVSCKASGYIFLTYWIN WVRQAPGQGLEWMGQIFPASDSTYYNQKFKGRVTI TADKSTSTAYMELSSLRSEDTAVYYCARSGPYSYYA GGYALDYWGQGTLVTVSS | 39 |
| GO11-A4 VH | QVQLVQSGAEVKKPGSSVKVSCKASGYIFLTYWIN WVRQAPGQGLEWMGQIFPASGSAYYAQKFQGRVTI TADKSTSTAYMELSSLRSEDTAVYYCARSGPYSYYA GGYALDYWGQGTLVTVSS | 40 |
| GO11-A5 VH | QVQLVQSGAEVKKPGSSVKVSCKASGYIFLTYWMN WVRQAPGQGLEWMGQIFPASGSAYYAQKFQGRVTI TVDKSTSTAYMELSSLRSEDTAVYYCARSGPYSYYA GGYALDYWGQGTLVTVSS | 41 |
| GO11-A6 VH | QVQLVQSGAEVKKPGSSVKVSCKASGYIFLTYWMN WVRQAPGQGLEWMGQIFPASGSAYYNQKFKGRVTI TADKSTSTAYMELSSLRSEDTAVYYCARSGPYSYYA GGYALDYWGQGTLVTVSS | 42 |
| GO11-A7 VH | QVQLVQSGAEVKKPGSSVKVSCKASGYIFLTYWIN WVRQAPGQGLEWMGQIFPASGSTYYNEKFKGRVTI TADKSTSTAYMELSSLRSEDTAVYYCARSGPYSYYA GGYALDYWGQGTLVTVSS | 43 |
| GO11-A1 VL | DIQMTQSPASLSASVGETVTITCRTSENINSYLAWYQ QKQGKSPQLLVHYAKTLAEGVPSRFSGSGSGTQFSL KINSLKPEDFGSYYCQHHYGTSLTFGAGTKLELK | 44 |
| GO11-A2 VL | DIQMTQSPSSLSASVGDRVTITCRASQSISSYLAWYQ QKPGKAPKLLIHYAKSLAEGVPSRFSGSGSGTDFTLT ISSLQPEDFATYYCQHHYGTSLTFGQGTKLEIK | 45 |
| GO11-A3 VL | DIQMTQSPSSLSASVGDRVTITCRASQSISSYLAWYQ QKPGKAPKLLIHYAKSLAEGVPSRFSGSGSGTDFTLT ISSLQPEDFATYYCQHHYGTSLTFGQGTKLEIK | 46 |
| GO11-A4 VL | DIQMTQSPSSLSASVGDRVTITCRASQSISSYLAWYQ QKPGKAPKLLIHYAKSLAEGVPSRFSGSGSGTDFTLT ISSLQPEDFATYYCQHHYGTSLTFGQGTKLEIK | 47 |
| GO11-A5 VL | DIQMTQSPSSLSASVGDRVTITCRASQSISSYLAWYQ QKPGKAPKLLIHYASSLAEGVPSRFSGSGSGTDFTLT ISSLQPEDFATYYCQHHYGTSLTFGQGTKLEIK | 48 |
| GO11-A6 VL | DIQMTQSPSSLSASVGDRVTITCRASQSISSYLAWYQ QKPGKAPKLLIHYASSLAEGVPSRFSGSGSGTDFTLT ISSLQPEDFATYYCQHHYGTSLTFGQGTKLEIK | 49 |

TABLE 3-continued

Amino acid sequences of VH and VL regions of additional exemplary anti-IL-1R3 antibodies that may be employed in an IgG4-P-FALA Fc.

| Antibody | Sequence | SEQ ID NO: |
|---|---|---|
| G011-A7 VL | DIQMTQSPSSLSASVGDRVTITCRASQSISSYLAWYQ QKPGKAPKLLIHYASSLAEGVPSRFSGSGSGTDFTLT ISSLQPEDFATYYCQHHYGTSLTFGQGTKLEIK | 50 |

In an alternative embodiment, an antibody is provided that specifically binds to IL-1R3 and comprises an antibody heavy chain variable (VH) domain amino acid sequence of SEQ ID NO: 24, an antibody light chain variable (VL) domain amino acid sequence of SEQ ID NO: 29, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 25, an antibody light chain variable (VL) domain amino acid sequence of SEQ ID NO: 30, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 25, an antibody light chain variable (VL) domain amino acid sequence of SEQ ID NO: 31, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 25, an antibody light chain variable (VL) domain amino acid sequence of SEQ ID NO: 32, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 26, an antibody light chain variable (VL) domain amino acid sequence of SEQ ID NO: 30, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 26, an antibody light chain variable (VL) domain amino acid sequence of SEQ ID NO: 31, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 26, an antibody light chain variable (VL) domain amino acid sequence of SEQ ID NO: 32, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 27, an antibody light chain variable (VL) domain amino acid sequence of SEQ ID NO: 30, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 27, an antibody light chain variable (VL) domain amino acid sequence of SEQ ID NO: 31, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 27, an antibody light chain variable (VL) domain amino acid sequence of SEQ ID NO: 32, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 28, an antibody light chain variable (VL) domain amino acid sequence of SEQ ID NO: 30, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 28, an antibody light chain variable (VL) domain amino acid sequence of SEQ ID NO: 31, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 28, an antibody light chain variable (VL) domain amino acid sequence of SEQ ID NO: 32, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 33, an antibody light chain variable (VL) domain amino acid sequence of SEQ ID NO: 34, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 35, an antibody light chain variable (VL) domain amino acid sequence of SEQ ID NO: 36, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 37, an antibody light chain variable (VL) domain amino acid sequence of SEQ ID NO: 44, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 38, an antibody light chain variable (VL) domain amino acid sequence of SEQ ID NO: 45, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 39, an antibody light chain variable (VL) domain amino acid sequence of SEQ ID NO: 46, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 40, an antibody light chain variable (VL) domain amino acid sequence of SEQ ID NO: 47, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 41, an antibody light chain variable (VL) domain amino acid sequence of SEQ ID NO: 48, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 42, an antibody light chain variable (VL) domain amino acid sequence of SEQ ID NO: 49, and an IgG4 Fc domain, wherein the IgG4 Fc domain comprises an F234A substitution, an L235A substitution, and an S228P substitution, according to EU numbering.

In an alternative embodiment, an antibody is provided that specifically binds to IL-1R3 and comprises an antibody heavy chain variable (VH) domain amino acid sequence of SEQ ID NO: 43, an antibody light chain variable (VL) domain amino acid sequence of SEQ ID NO: 50, and an IgG4 Fc domain, wherein the IgG4 Fc domain comprises an F234A substitution, an L235A substitution, and an S228P substitution, according to EU numbering.

II. Antibody Production and Further Aspects Related Thereto

Antibody production can be performed by any technique known in the art. Antibodies may be produced by chemical synthesis or by expression of genes encoding the antibodies in host cells, e.g., a cell line such as Chinese hamster ovary (CHO) cell line, or a human embryonic kidney (HEK) cell line.

The third aspect relates to an isolated nucleic acid molecule encoding the antibody of the first aspect. For further details on the antibody of the first aspect, see the disclosure in Section I above.

The fourth aspect relates to an expression vector comprising the nucleic acid molecule of the third aspect.

The fifth aspect relates to a host cell comprising the expression vector of the fourth aspect. In an embodiment, the host cell comprises a nucleic acid molecule encoding the antibody of the first aspect. In an embodiment, the host cell is a Chinese hamster ovary (CHO) cell, preferably wherein the host cell is a CHO DXB11 cell.

The sixth aspect relates to a method of manufacturing the antibody of the first aspect comprising the steps of: (i) optionally transfecting a host cell using the isolated nucleic acid molecule of third aspect or the expression vector of the fourth aspect; (ii) cultivating the host cell under conditions allowing expression of the antibody; (iii) recovering the antibody; and (iv) optionally further purifying and/or modifying and/or formulating the antibody.

In an embodiment, the method of manufacturing comprises:
(i) transfecting a host cell being a Chinese hamster ovary (CHO) cell using the isolated nucleic acid molecule of the third aspect or the expression vector of fourth aspect, preferably wherein the host cell is a CHO DXB11 cell.

In an embodiment of the method of manufacturing, the expression level of the antibody is greater than the expression level of an anti-IL-1R3 antibody comprising a human IgG1 Fc region, preferably wherein the human IgG1 Fc region comprises amino acid substitutions L234A and L235A, according to EU numbering. In an embodiment of the method of manufacturing, the expression level of the antibody is greater than the expression level of an anti-IL-1R3 antibody comprising the human IgG1 Fc region amino acid sequence of SEQ ID NO: 18. In an embodiment of the method of manufacturing, the expression level of the antibody is greater than the expression level of an anti-IL-1R3 antibody comprising:
the human IgG1 Fc region amino acid sequence of SEQ ID NO: 18, and
light chain amino acid sequence of SEQ ID NO: 4.
In an embodiment of the method of manufacturing, the expression level of the antibody is greater than the expression level of an anti-IL-1R3 antibody comprising:
the human IgG1 Fc region amino acid sequence of SEQ ID NO: 18, and
light chain amino acid sequence of SEQ ID NO: 2.

In an embodiment, the method of manufacturing comprises:
(iv) further purifying and/or modifying and/or formulating the antibody. In at least one embodiment, the formulating comprises combining the antibody with a pharmaceutically acceptable diluent, carrier or excipient. In an embodiment, step (iv) results in pharmaceutical composition according to the second aspect.

In an embodiment, the method of manufacturing produces an antibody according to the first aspect. In an embodiment of the method of manufacturing, the expression level of the antibody is greater than the expression level of the same anti-IL-1R3 antibody differing only in that the heavy chain is a human IgG1 Fc region having amino acid substitutions L234A and L235A, according to EU numbering.

The seventh aspect relates to an antibody produced by the method of manufacturing according to the sixth aspect. In an embodiment, the antibody produced is according to the first aspect.

A polynucleotide encoding a humanized mAb, or a humanized mAb fragment (e.g., an anti-IL-1R3 antibody or fragment thereof as disclosed herein) is isolated and inserted into a replicable construct or vector such as a plasmid for further propagation or expression in a host cell. Constructs or vectors (e.g., expression vectors) suitable for the expression of a humanized mAb, or a humanized mAb fragment (e.g., an anti-IL-1R3 antibody or fragment thereof) according to the described embodiments are available in the art. A variety of vectors are available, including vectors which are maintained in single copy or multiple copies in a host cell, or which become integrated into the host cell's chromosome(s). The constructs or vectors can be introduced into a suitable host cell, and cells which express a humanized immunoglobulin can be produced and maintained in culture. A single vector or multiple vectors can be used for the expression of a humanized immunoglobulin.

Polynucleotides encoding a humanized mAb, or a humanized mAb fragment (e.g., an anti-IL-1R3 antibody or fragment thereof as disclosed herein) are readily isolated and sequenced using conventional procedures (e.g., oligonucleotide probes). Vectors that may be used include plasmid, virus, phage, transposons, minichromosomes of which plasmids are a typical embodiment. Generally, such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and introduced (e.g., by transformation, transfection, electroporation or transduction) into the same host cell concurrently or sequentially or, if desired, both the heavy chain and light chain can be inserted into the same vector prior to such introduction.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for prokaryotic and eukaryotic hosts are available. Prokaryotic promoters include lac, tac, T3, T7 promoters for *E. coli;* 3-phosphoglycerate kinase or other glycolytic enzymes e.g., enolase, glyceraldehyde 3-phosphate dehydrogenase, hexokinase, pyruvate decarboxylase, phosphofructokinase, glucose 6 phosphate isomerase, 3-phosphoglycerate mutase and glucokinase. Eukaryotic promoters include inducible yeast promoters such as alcohol dehydrogenase 2, isocytochrome C, acid phosphatase, metallothionein and enzymes responsible for nitrogen metabolism or maltose/galactose utilization; RNA polymerase II promoters including viral promoters such as polyoma, fowlpox and adenoviruses (e.g., adenovirus 2), bovine papilloma virus, avian sarcoma virus, cytomegalovirus (in particular, the immediate early gene promoter), retrovirus, hepatitis B virus, actin, Rous sarcoma virus (RSV) promoter and the early or late Simian virus 40 and non-viral promoters such as EF-1 alpha (Mizushima and Nagata (1990) Nucleic Acids Res. 18(17):5322). Those of skill in the art will be able to select the appropriate promoter for expressing a humanized antibody or portion thereof.

Where appropriate, e.g., for expression in cells of higher eukaryotes, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaryotic cell virus such as SV40 enhancer, cytomegalovirus early promoter enhancer, polyoma enhancer, baculoviral enhancer or murine IgG2a locus (see, for example, Kallmeier & Gay WO2004009823). Whilst such enhancers are often located on the vector at a site upstream to the promoter, they can also be located elsewhere e.g., within the untranslated region or downstream of the polyadenylation signal. The choice and positioning of enhancer may be based upon compatibility with the host cell used for expression.

In addition, the vectors (e.g., expression vectors) may comprise a selectable marker for selection of host cells carrying the vector, and, in the case of a replicable vector, an origin of replication. Genes encoding products which confer antibiotic or drug resistance are common selectable markers and may be used in prokaryotic (e.g., f3-lactamase gene (ampicillin resistance), tet gene (tetracycline resistance) and eukaryotic cells (e.g., neomycin (G418 or geneticin), gpt (mycophenolic acid), ampicillin, or hygromycin 5 resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

In eukaryotic systems, polyadenylation and termination signals are operably linked to polynucleotide encoding the antibody described herein. Such signals are typically placed 3' of the open reading frame. In mammalian systems, non-limiting examples of polyadenylation/termination signals include those derived from growth hormones, elongation factor-1 alpha and viral (e.g., SV40) genes or retroviral long terminal repeats. In yeast systems, non-limiting examples of polyadenylation/termination signals include those derived from the phosphoglycerate kinase (PGK) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon compatibility with the host cell used for expression. In addition to the above, other features that can be employed to enhance yields include chromatin remodeling elements, introns and host cell specific codon modification. The codon usage of the antibodies described herein can be modified to accommodate codon bias of the host cell such to augment transcript and/or product yield (e.g., Hoekema, A. et al. (1987) Mol. Cell Biol. 7(8):2914-24). The choice of codons may be based upon compatibility with the host cell used for expression.

This disclosure thus relates to isolated nucleic acid molecules that encode the humanized immunoglobulins, or heavy or light chains, thereof. This disclosure also relates to isolated nucleic acid molecules that encode an antigen-binding portion of the immunoglobulins and their chains.

A humanized mAb, or a humanized mAb fragment (e.g., an anti-IL-1R3 antibody or fragment thereof) can be produced, for example, by the expression of one or more recombinant nucleic acids encoding the antibody in a suitable host cell, e.g., CHO cell line. The host cell can be produced using any suitable method. For example, the expression constructs (e.g., one or more vectors, e.g., a mammalian cell expression vector) described herein can be introduced into a suitable host cell, and the resulting cell can be maintained (e.g., in culture) under conditions suitable for expression of the construct(s) or vector(s). Host cells can be prokaryotic, including bacterial cells such as E. coli (e.g., strain DH5α™) (Invitrogen, Carlsbad, CA), PerC6 (Crucell, Leiden, NL), B. subtilis and/or other suitable bacteria; eukaryotic cells, such as cells of higher eukaryotes such as those from mammals (e.g., COS cells, such as COS-1 (ATCC Accession No. CRL-1650) and COS-7 (ATCC Accession No. CRL-1651), CHO (e.g., ATCC Accession No. CRL-9096), CHO DG44 (Urlaub, G. and Chasin, L. A. (1980) Proc. Natl. Acad. Sci. USA, 77(7):4216-4220), 293 (ATCC Accession No. CRL-1573), HEK, HeLa (ATCC Accession No. CCL-2), CVI (ATCC Accession No. CCL-70), WOP (Dailey, L., et al. (1985) J. Virol., 54:739-749), 3T3, 293T (Pear, W. S., et al. (1993) Proc. Natl. Acad. Sci. U.S.A., 90:8392-8396), NSO cells, SP2/0 cells, HuT 78 cells, and the like, or plants (e.g., tobacco, lemna (duckweed), and algae). See, for example, Ausubel, F. M. et al., eds. Current Protocols in Molecular Biology, Greene Publishing Associates and John Wiley & Sons Inc. (1993). In some embodiments, the host cell is not part of a multicellular organism, e.g., it is an isolated host cell or is part of a cell culture.

Host cells may be cultured in spinner flasks, shake flasks, roller bottles, wave reactors (e.g., System 1000 from wavebiotech.com) or hollow fiber systems, but it is preferred for large scale production that stirred tank reactors or bag reactors (e.g., Wave Biotech, Somerset, New Jersey USA) are used particularly for suspension cultures. Stirred tank reactors can be adapted for aeration using e.g., spargers, baffles or low shear impellers. For bubble columns and airlift reactors, direct aeration with air or oxygen bubbles maybe used. Where the host cells are cultured in a serum-free culture medium, the medium can be supplemented with a cell protective agent such as pluronic F-68 to help prevent cell damage as a result of the aeration process. Depending on the host cell characteristics, microcarriers may be used as growth substrates for anchorage dependent cell lines, or the cells may be adapted to suspension culture. The culturing of host cells, particularly vertebrate host cells, may utilize a variety of operational modes such as batch, fed-batch, repeated batch processing (see, Drapeau et al. (1994) Cytotechnology 15:103-109), extended batch process or perfusion culture. Although recombinantly transformed mammalian host cells may be cultured in serum-containing media such media comprising fetal calf serum (FCS), it is preferred that such host cells are cultured in serum-free media such as disclosed in Keen et al. (1995) Cytotechnology 17:153-163, or commercially available media such as ProCHO™ or UltraCHO™ (Cambrex NJ, USA), supplemented where necessary with an energy source such as glucose and synthetic growth factors such as recombinant insulin. The serum-free culturing of host cells may require that those cells are adapted to grow in serum-free conditions. One adaptation approach is to culture such host cells in serum containing media and repeatedly exchange 80% of the culture medium for the serum-free media so that the host cells learn to adapt in serum-free conditions (see, e.g., Scharfenberg, K. et al. (1995) Animal Cell Technology: Developments Towards the 21st Century (Beuvery, E. C. et al., eds), pp. 619-623, Kluwer Academic publishers).

A humanized mAb, or a humanized mAb fragment (e.g., an antibody or fragment thereof) according to the described embodiments may be secreted into the medium and recovered and purified therefrom using a variety of techniques to provide a degree of purification suitable for the intended use. For example, the use of a humanized mAb, or a humanized mAb fragment (e.g., an anti-IL-1R3 antibody or fragment thereof) for the treatment of human subjects typically mandates at least 95% purity as determined by reducing SDS-PAGE, more typically 98% or 99% purity, when compared to the culture media comprising the therapeutic antibodies. In the first instance, cell debris from the culture media can be removed using centrifugation followed by a clarification step of the supernatant using e.g., microfiltration, ultrafiltration and/or depth filtration. Alternatively, a humanized mAb, or a humanized mAb fragment (e.g., an anti-IL-1R3 antibody or fragment thereof) can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC) (see, U.S. Pat. No. 5,429,746) are available. In one embodiment, a humanized mAb, or a humanized mAb fragment (e.g., an anti-IL-1R3 antibody or fragment thereof), following various clarification steps, are captured using Protein A or Protein G affinity chromatography followed by further chromatography steps such as ion exchange and/or HA chromatography, anion or cation exchange, size exclusion chromatography and ammonium sulphate precipitation. Various virus removal steps may also be employed (e.g., nanofiltration using, e.g., a DV-20 filter). Following these various steps, a purified preparation comprising at least 10 mg/mL or greater, e.g., 100 mg/mL or greater of the antibody described herein is provided and, therefore, forms another embodiment described herein. Concentration to 100 mg/mL or greater can be generated by ultracentrifugation. Such preparations are substantially free of aggregated forms of antibodies.

Bacterial systems are particularly suited for the expression of antibody fragments. Such fragments are localized intracellularly or within the periplasm. Insoluble periplasmic proteins can be extracted and refolded to form active proteins according to methods known to those skilled in the art, see, Sanchez et al. (1999) J. Biotechnol. 72:13-20; Cupit, P. M. et al. (1999) Lett. Appl. Microbiol. 29:273-277.

The fifth aspect relates to a host cell comprising the expression vector of the fourth aspect. The present disclosure also relates to cells (host cells) comprising a nucleic acid, e.g., a vector, described herein (e.g., an expression vector). For example, a nucleic acid (i.e., one or more nucleic acids) encoding the heavy and light chains of a humanized immunoglobulin according to the described embodiments, or a construct (e.g., one or more constructs, e.g., one or more vectors) comprising such nucleic acid(s), can be introduced into a suitable host cell by a method appropriate to the host cell selected (e.g., transformation, transfection, electroporation, infection), with the nucleic acid(s) being, or becoming, operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded humanized antibody can be isolated, for example, from the host cells, culture medium, or milk. This process encompasses expression in a host cell (e.g., a mammary gland cell) of a transgenic animal or plant (e.g., tobacco) (see, e.g., Lonberg & Kay in WO1992003918).

Batch consistency and comparability are highly relevant to the successful pharmaceutical development of recombinant mAbs and related products. Small structural modifications can result in variants (or proteoforms) differing in size, charge or hydrophobicity. These modifications may or may not impact the stability, pharmacokinetics, and efficacy of the recombinant mAbs. The presence of the same type of modifications as found in endogenous immunoglobulin G (IgG) can substantially lower the safety risks of mAbs.

The following post-translational and physico-chemical modifications can occur in recombinant mAbs and are a function of the expression system used: N-terminal modifications (N-terminal pyroglutamate, incomplete removal of signal peptide, truncation); asparagine deamidation; aspartate isomerization; presence of succinimide; degradation/oxidation of amino acid residues (especially methionine and tryptophan); cysteine related modifications (free cysteine residues, alternative disulfide bond linkages (scrambling), trisulfide bonding, formation of thioether, cysteine racemization); glycosylation; glycation; C-terminal modifications (clipping of C-terminal lysine, amidation, sequence variation due to inherent errors in transcription or translation); and rare chemical modifications (such as oxidative carbonylation, histidine-histidine cross-linking, tyrosine sulfation, modification of heavy chain N-termini by maleuric acid, modification of N-terminal primary amine or lysine side chain by citric acid or its degradation products, and O-fucosylation of a serine residues).

III. Pharmaceutical Compositions and Methods of Administration of Anti-IL-1R3 Antibodies The second aspect relates to a pharmaceutical composition comprising the antibody of the first aspect and a pharmaceutically acceptable diluent, carrier or excipient. In certain embodiments, pharmaceutical compositions are provided comprising a humanized mAb, or a humanized mAb fragment (e.g., an anti-IL-1R3 antibody or fragment thereof) described herein, or a ligand or ligands identifiable by an assay method as defined in a previous aspect of the disclosure are provided. Ligands may be immunoglobulins, peptides, nucleic acids or small molecules, as discussed herein. They are referred to, in the following discussion, as "compounds."

In an embodiment, the pharmaceutical composition described herein is a composition of matter comprising a compound or compounds capable of modulating T-cell activity as an active ingredient. The compound may be in the form of any pharmaceutically acceptable salt, or e.g., where appropriate, is an analog, free base form, tautomer, enantiomer racemate, or combination thereof. The active ingredients of a pharmaceutical composition comprising the active ingredient described herein are contemplated to exhibit therapeutic activity, for example, in the treatment of graft-versus-host disease, when administered in an amount which depends on the particular case.

In certain embodiments, a pharmaceutical composition comprises a humanized mAb, or a humanized mAb fragment (e.g., an anti-IL-1R3 antibody or fragment thereof) described herein, and pharmaceutically acceptable diluent, carrier or excipient. In at least one embodiment, the pharmaceutical composition is an aqueous composition.

In certain embodiments, one or more compounds described in this disclosure may be used in combination with any art recognized compound known to be suitable for treating the particular indication in treating any of the aforementioned conditions. Accordingly, one or more compounds described herein may be combined with one or more art recognized compounds known to be suitable for treating the foregoing indications such that a convenient, single composition can be administered to the subject. Dosage regimens may be adjusted to provide the optimum therapeutic response.

For example, several divided doses may be administered daily or the dose may be proportionally reduced as indicated by the exigencies of the therapeutic situation.

The active ingredient may be administered in a convenient manner such as by the oral, intravenous (where water soluble), intramuscular, subcutaneous, intranasal, intradermal or suppository routes or implanting (e.g., using slow-release molecules). In the case of a transplant, the active ingredient may also be used to treat cells, tissues, or organs being transplanted into a patient prior to the transplantation. This may be done in order to prevent, decrease the likelihood, or lessen the symptoms of, for example, graft versus host disease.

Depending on the route of administration, the active ingredient may be required to be coated in a material to protect said ingredients from the action of enzymes, acids and other natural conditions which may inactivate said ingredient.

In order to administer the active ingredient by means other than parenteral administration, it will be coated by, or administered with, a material to prevent its inactivation. For example, the active ingredient may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water emulsions as well as conventional liposomes.

The active ingredient may also be administered parenterally or intraperitoneally.

Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In certain cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient in the required amount in the appropriate solvent with several of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Various other materials may be present as coatings or to otherwise modify the physical form of the dosage unit. Of course, any material used in preparing any dosage unit form should be pharmaceutically pure and substantially non-toxic in the amounts employed. In addition, the active ingredient may be incorporated into sustained-release preparations and formulations.

As used herein "pharmaceutically acceptable diluent, carrier or excipient" includes any and all solvents, dispersion media, coatings, antibacterial and antifungal agents, isotonic and absorption delaying agents and the like. In certain embodiments the pharmaceutically acceptable carrier or diluent is an aqueous fluid. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms described herein are dictated by and directly dependent on (a) the unique characteristics of the active material and the particular therapeutic effect to be achieved, and (b) the limitations inherent in the art of compounding such as active material for the treatment of disease in living subjects having a disease or condition in which bodily health is impaired. The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

In order to facilitate delivery of peptide compounds, including antibodies, to cells, peptides may be modified in order to improve their ability to cross a cell membrane. For example, Chang et al. in U.S. Pat. No. 5,149,782 (Tanox Biosystems, Inc.) discloses the use of fusogenic peptides, ion-channel forming peptides, membrane peptides, long-chain fatty acids and other membrane blending agents to increase protein transport across the cell membrane. These and other methods are also described in Wallach et al. in WO1997037016 and Low et al. in U.S. Pat. No. 5,108,921, incorporated herein by reference.

In a further aspect there is provided the active ingredient described herein for use in the treatment of disease either alone or in combination with art recognized compounds known to be suitable for treating the particular indication. Consequently, there is provided the use of an active ingredient described herein for the manufacture of a medicament for the treatment of disease associated with an aberrant immune response.

Moreover, there is provided a method for treating a condition associated with an aberrant immune response, comprising administering to a subject a therapeutically effective amount of antibody or antigen binding fragment thereof.

IV: Method for Treating a Disease or Disorder

The eighth aspect relates to the antibody of the first aspect for use in treating a disease or disorder in a subject in need thereof, preferably wherein the disease or disorder is an autoimmune or autoinflammatory disease or disorder.

The ninth aspect relates to the pharmaceutical composition of the second aspect for use in treating a disease or disorder in a subject in need thereof, preferably wherein the disease or disorder is an autoimmune or autoinflammatory disease or disorder.

The tenth aspect relates to a method for treating a disease or disorder in a subject in need thereof comprising administering to the subject the antibody of the first aspect or the pharmaceutical composition of the second aspect.

Another aspect relates to the use of the antibody of the first aspect or the pharmaceutical composition of the second aspect in the manufacture of a medicament for treating a disease or disorder in a subject in need thereof.

Another aspect relates to the use of the antibody of the first aspect or the pharmaceutical composition of the second aspect for treating a disease or disorder in a subject in need thereof.

In the light of the evidence presented, a person of skill in the art would understand that the antibody of the present disclosure could be used for the prevention, treatment, alleviation, detection and/or diagnosis of inflammatory and/or fibrotic and/or neoplastic diseases disorders due to its ability to inhibit signaling of IL-1α, IL-1β, IL-33, IL-36α, IL-36β and IL-36γ, thereby targeting several IL-dependent pathways at the same time.

An embodiment relates to the antibody of the first aspect or the pharmaceutical composition of the second aspect, for use in treating a disease or disorder in a subject in need thereof, wherein the disease or disorder is an inflammatory and/or fibrotic disease or disorder, preferably an inflammatory skin disease.

In some embodiments, said disease or disorder is an inflammatory and/or fibrotic disease or disorder. In some embodiments, said disease or disorder is an inflammatory and/or fibrotic disease or disorder, wherein the inflammatory and/or fibrotic disease or disorder is selected from the group consisting of rheumatoid arthritis, all types of arthritis, psoriatic arthritis, all types of juvenile arthritis, including systemic onset juvenile idiopathic arthritis (SOJIA), osteoarthritis, familial cold auto-inflammatory syndrome (FCAS), Muckle-Wells disease, neonatal onset multi-system inflammatory disease (NOMID), familial Mediterranean fever (FMF), pyogenic arthritis pyoderma gangrenosum and acne (PAPA) syndrome, adult onset Still's disease, hyper IgD syndrome, type 2 diabetes mellitus, macrophage activation syndrome, TNF receptor-associated periodic syndrome, Blau disease, ankylosing spondylitis, Sweets disease, lupus arthritis, Alzheimer's disease, psoriasis, asthma, allergy, atherosclerosis, sarcoidosis, atopic dermatitis, systemic lupus erythematosus, bullous pemphigoid, type I diabetes mellitus, chronic obstructive pulmonary disease (COPD), *Helicobacter pylori* gastritis, inflammatory bowel disease (including ulcerative colitis), hepatitis, hepatitis C, ischaemia-reperfusion injury, multiple sclerosis, Neisserial or pneumococcal meningitis, tuberculosis, Behcet's syndrome, septic shock, graft versus host disease, adult T cell leukaemia, multiple myeloma, periodontitis, obesity and obesity-related diseases (for example, metabolic syndrome, cardiomegaly, congestive heart failure, myocardial infarction, varicose veins, polycystic ovarian syndrome, gastroesophageal reflux disease (GERD), fatty liver disease, colorectal cancer, breast cancer, uterine cancer, chronic renal failure, stroke and hyperuricemia), intervertebral disc disease, irritable bowel syndrome, Schnitzler syndrome, allergy/atopic dermatitis, acne inversa (hidradenitis suppurativa), cardiac fibrosis, cardiovascular diseases, cryopyin-associated periodic syndromes, cystic fibrosis, Goodpasture's syndrome, Guillain-Barre syndrome, kidney fibrosis, liver fibrosis, lung fibrosis (pulmonary fibrosis), skin fibrosis (dermal fibrosis), myocarditis, autoimmune myocarditis, organ dysfunction associated with organ transplantation, pancreatitis, peritonitis, uveitis, vasculitis, pneumonia, pulmonary hypertension, sclerodermatous chronic graft-versus-host disease, sepsis, Sjögren's syndrome, Takayasu's arteritis and gout.

In at least one embodiment, the disease or disorder is an inflammatory condition such as metabolic rheumatic disorder associated with hyperuricemia. The metabolic rheumatic disorder can be selected from the group consisting of gout, pseudogout, drug-induced gout and chronic active (refractory) gout.

In at least one embodiment, the disease or disorder is an IL-1-dependent inflammatory disease. For example, the disease can be a systemic or a local inflammatory disease. In at least one embodiment, the disease or disorder is selected from the group consisting of Schnitzler Syndrome, Behçet's disease, secondary amyloidosis, Henoch-Schonlein purpura, idiopathic recurrent pericarditis, systemic-onset juvenile idiopathic arthritis, adult onset Still's disease (AOSD), macrophage activation Syndrome, Sweet's syndrome/neutrophilic dermatoses (acute febrile neutrophilic dermatosis), neutrophilic panniculitis, Erdheim-Chester disease (histiocytosis), SAPHO syndrome (synovitis, acne, pustulosis, hyperostosis, osteitis), PFAPA (periodic fever, aphtous stomatitis, pharyngitis, adenitis), multicentric Castleman disease, Jessner-Kanof disease, primary Sjoegren syndrome (fatigue), Kawasaki disease, colitis in chronic granulomatous disease, hidradenitis suppurativa (acne inversa), autoimmune inner ear disease and severe traumatic brain injury. In at least one embodiment, the disease or disorder is a hereditary systemic inflammatory diseases such as familial Mediterranean fever (FMF), cryopyrin associated periodic syndrome (CAPS), tumour necrosis factor (TNF) receptor 1-associated periodic syndrome (TRAPSa), hyper IgD syndrome (HIDS), PAPA (pyogenic arthritis, pyoderma gangrenosum and acne) syndrome, PASH (pyoderma gangrenosum, acne and suppurative hidradenitis) syndrome, PAPASH (pyogenic arthritis, acne, pyoderma gangrenosum and suppurative hidradenitis) syndrome, deficiency of interleukin 1 receptor antagonist (DIRA), Blau syndrome/granulomatous arthritis, mevalonate kinase deficiency, Majeed syndrome, and NLRP12 (nucleotide-binding leucine-rich repeat-containing receptor 12) autoinflammatory syndrome.

In certain embodiments, the disease or disorder is selected from the group consisting of atopic dermatitis, acne inversa (hidradenitis suppurativa), pyoderma syndrome, pyoderma gangrenosum, pustular psoriasis, asthma, idiopathic pulmonary fibrosis, peritonitis, rheumatoid arthritis, and chronic obstructive pulmonary disease (COPD). In at least one embodiment, the disease or disorder is a pyoderma syndrome. In at least one embodiment, the disease or disorder is pyoderma gangrenosum.

In at least one embodiment, the disease or disorder is asthma. In at least one embodiment, the disease or disorder is idiopathic pulmonary fibrosis. In certain embodiments, the disease or disorder is selected from the group consisting of hidradenitis suppurativa (acne inversa) and COPD, preferably hidradenitis suppurativa (acne inversa). In at least one embodiment, the disease or disorder is atopic dermatitis. In certain embodiments, the disease or disorder is a respiratory disease. In certain embodiments, the disease or disorder is an inflammatory skin disease.

An embodiment relates to the antibody of the first aspect or the pharmaceutical composition of the second aspect, for use in treating a disease or disorder in a subject in need thereof, wherein the disease or disorder is a neoplastic disease or disorder.

In some embodiments, said disease or disorder is a neoplastic disease or disorder, wherein the neoplastic disease or disorder is a hematologic disease or disorder or a solid tumour. In some embodiments, said neoplastic disease or disorder is a hematologic disease, wherein the neoplastic hematologic disease or disorder is selected from the group consisting of chronic myeloid leukemia (CML), myeloproliferative disorders (MPD), myelodysplastic syndrome (MDS), acute lymphoblastic leukemia (ALL) and acute myeloid leukemia (AML). In some embodiments, said neoplastic disease or disorder is a solid tumor, wherein the solid tumour is selected from the group consisting of prostate cancer, breast cancer, lung cancer, colon cancer, colorectal cancer, melanomas, bladder cancer, brain/CNS cancer, cancer of urinary organs, biliary tract cancer (also known as bile duct cancer), cervical cancer, oesophageal cancer, gastric cancer, head/neck cancer (head and neck squamous cell carcinoma), kidney cancer, liver cancer, lymphomas, ovarian cancer, pancreatic cancer, sarcomas, skin cancer and uterus cancer. Preferably, the neoplastic disease or disorder is breast cancer, colon cancer, lung cancer, pancreatic cancer, liver cancer, non-small-cell-lung cancer, colorectal cancer, stomach cancer, gastric cancer, estrogen-receptor positive breast cancer, head and neck squamous cell carcinoma, Mesothelioma, Gall bladder cancer, ovarian cancer, bladder cancer, prostate cancer, Thyroid cancer, Hodgkin disease, MALT lymphoma, salivary gland cancer, or melanoma.

A further aspect relates to a method for the treatment of a subject, wherein the subject is characterized in being resistant or showing insufficient response to treatment with one or more cytotoxic, cytostatic or targeted anti-cancer agents. In an embodiment, the antibody of the first aspect is administered in combination with one or more cytotoxic, cytostatic or targeted anti-cancer agents. In an embodiment, the antibody of the first aspect is administered simultaneously with one or more cytotoxic, cytostatic or targeted anti-cancer agents. In an embodiment, the antibody of the first aspect is administered sequentially with one or more cytotoxic, cytostatic or targeted anti-cancer agents. In the latter case, it is preferred that the antibody of the first aspect is administered after treatment with one or more cytotoxic, cytostatic or targeted anti-cancer agents. The cytotoxic or cytostatic anti-cancer agents can be taxanes, anthracyclins, alkylating agents, histone deacetylase inhibitors, topoisomerase inhibitors, kinase inhibitors, nucleotide analogs, peptide antibiotics, and platinum-based agents.

In at least one embodiment, the disease or disorder is a cancer-associated chronic inflammation.

A further aspect relates to the non-therapeutic use of the antibody of the first aspect or the pharmaceutical composition of the second aspect for cosmetic purposes.

The examples provided below are for the purposes of illustration only, and should not be considered limiting on the compositions and methods described herein.

EXAMPLES

Example 1: Generation of Anti-IL-1R3 IgG4-P-FALA Antibody

An anti-IL-1R3 mAb was humanized by CDR grafting using recombinant DNA technology. The human IgG backbone was either IgG4 containing P-FALA (S228P, F234A, L235A) mutations in the Fc region or IgG1 backbone containing LALA (L234A, L235A) mutations in the Fc region. Resulting vectors encoded a heavy chain and light chain of the humanized antibodies anti-IL-1R3-IgG4-P-FALA or anti-IL-1R3-IgG1-LALA.

Example 2: Selection of CHO Cell Line Clones Expressing Anti-IL-1R3 IgG4-P-FALA Antibody in CHO Cell Line The CHO DXB11 host line was derived directly from the CHO DXB11 cell line (Urlaub and Chasin, 1980, Proc Natl Acad Sci USA) by adapting the CHO DXB11 cell line eventually to a commercial animal-component free and chemically-defined media (CD DG44) followed by subcloning. A host master cell bank was created and this cell bank was used to generate host working cell banks (WCBs). An WCB was used as the cell source for generation of the anti-IL-1R3 expressing cell line.

The host cell line is propagated in a commercial medium (CD DG44, ThermoFisher Scientific) supplemented with 4 mM L-glutamine and 0.18% (v/v) poloxamer 188 (Pluronic F68, ThermoFisher Scientific). The cells are grown at 37° C., 5% $CO_2$, 80% relative humidity as suspension culture. The host cell line is cryopreserved in this CD DG44 growth medium (CD DG44, 4 mM L-glutamine, 0.18% (v/v) poloxamer 188) with 7% (v/v) dimethyl sulfoxide (DMSO) as cryoprotectant.

TABLE 4

Nucleotide sequences of each portion of the expression cassettes/vectors used to express anti-IL-1R3 antibody

| Portion/region | Sequence | SEQ ID NO: |
|---|---|---|
| DNA encoding heavy chain (HC) of IgG4-P-FALA | ATGGGCTGGTCCTGCATCATCCTGTTTCTGGTG GCTACCGCTACCGGCGTGCACTCTGAAGTGCA GCTGGAAGAATCTGGCGGCAGACTGGTGCAGC CTGGCACATCTCTGAGACTGTCTTGTGCCGTGT CCGGCTTCTCCCTGTCCTCCTACGATATGTCCT GGGTCCGACAGGCTCCTGGCAAAGGACTGGAA TGGGTGTCCACCATCTACATCGGCGGAACAAC CGCCTACGCCTCCTGGCCTAAGGGCAGATTCA CCATCTCCAAGACCAACTCCAAGAACACCCTG TACCTGCAGATGAACTCCCTGAGAGCCGAGGA TACCGCCGTGTACTTCTGCGCTAGACTGCAGG GCGCCAACTACTACAACTCTCTGGCTCTGTGG GGCCAGGGCACACTGGTTACAGTGTCCTCCGC TTCCACCAAGGGACCCTCTGTGTTTCCTCTGGC TCCTTGCTCCAGATCCACCTCCGAGTCTACAGC TGCTCTGGGCTGCCTGGTCAAGGACTACTTTCC TGAGCCTGTGACCGTGTCCTGGAACTCTGGCG CTCTGACATCTGGCGTGCACACCTTTCCAGCTG TGCTGCAGTCCTCCGGCCTGTACTCTCTGTCCT CTGTCGTGACCGTGCCTTCCTCTAGCCTGGGCA CCAAGACCTACACCTGTAATGTGGACCACAAG CCTTCCAACACCAAGGTGGACAAGCGCGTGGA ATCTAAGTACGGCCCTCCTTGTCCTCCATGTCC TGCTCCAGAAGCTGCTGGCGGCCCCATCAGTGT TTCTGTTCCCTCCAAAGCCTAAGGACACCCTG ATGATCTCTCGGACCCCTGAAGTGACCTGCGT GGTGGTGGATGTGTCCCAAGAGGATCCCGAGG TGCAGTTCAATTGGTACGTGGACGGCGTGGAA GTGCACAACGCTAAGACCAAGCCTAGAGAGG AACAGTTCAACTCCACCTACAGAGTGGTGTCC GTGCTGACCGTGCTGCATCAGGATTGGCTGAA CGGCAAAGAGTACAAGTGCAAGGTGTCCAACA AGGGCCTGCCTTCCAGCATCGAAAAGACCATC AGCAAGGCCAAGGGCCAGCCTAGGGAACCCC AGGTTTACACCCTGCCTCCAAGCCAAGAGGAA ATGACCAAGAACCAGGTGTCCCTGACCTGCCT CGTGAAGGGCTTCTACCCTTCCGATATCGCCGT GGAATGGGAGAGCAATGGCCAGCCTGAGAAC AACTACAAGACAACCCCTCCTGTGCTGGACTC | 19 |

TABLE 4-continued

Nucleotide sequences of each portion of the
expression cassettes/vectors
used to express anti-IL-1R3 antibody

| Portion/region | Sequence | SEQ ID NO: |
|---|---|---|
| | CGACGGCAGCTTCTTCCTGTATTCCCGCCTGAC<br>CGTGGACAAGTCCAGATGGCAAGAGGGCAAC<br>GTGTTCTCCTGCTCCGTGATGCACGAGGCCCTG<br>CACAATCACTACACCCAGAAGTCCCTGTCTCT<br>GTCCCTGGGCTAA | |
| DNA encoding light chain of IL-1R3 IgG4 P-FALA | ATGGGCTGGTCCTGCATCATCCTGTTTCTGGTG<br>GCTACCGCTACCGGCGTGCACTCTGATGTGCA<br>GATGACCCAGTCTCCTTCCAGCCTGTCTGCCTC<br>TGTGGGCGACAGAGTGACCATCACCTGTCAGG<br>CCAGCCAGTCTATCTACTCCTTCCTGTCCTGGT<br>ATCAGCAGAAGCCCGGCCAGGCTCCTAAGCTG<br>CTGATCTACGCTGCCTCCGACCTGGAATCTGG<br>CGTGCCCTCTAGATTCTCCGGCTCTGGCTCTGG<br>CACCGACTTTACCCTGACAATCTCCAGCCTGC<br>AGCCTGAGGACTTCGCCACCTACTACTGCCAG<br>TCCAACTACATCATCGACTACGGCGCCTTTGG<br>CCAGGGCACCAAGGTGGTCATCAAGAGAACA<br>GTGGCCGCTCCTTCCGTGTTCATCTTCCCACCT<br>TCCGACGAGCAGCTGAAGTCCGGCACAGCTTC<br>TGTCGTGTGCCTGCTGAACAACTTCTACCCTCG<br>GGAAGCCAAGGTGCAGTGGAAGGTGGACAAT<br>GCCCTGCAGTCCGGCAACTCCCAAGAGTCTGT<br>GACCGAGCAGGACTCCAAGGACAGCACCTATA<br>GCCTGTCCTCCACACTGACCCTGTCCAAGGCC<br>GACTACGAGAAGCACAAGGTGTACGCCTGCGA<br>AGTGACCCATCAGGGCCTGTCTAGTCCCGTGA<br>CCAAGTCTTTCAACCGGGGCGAGTGTTGA | 20 |
| SV40 early promoter [p(A)] | GATCATAATCAGCCATACCACATTTGTAGAGG<br>TTTTACTTGCTTTAAAAAACCTCCCACACCTCC<br>CCCTGAACCTGAAACATAAAATGAATGCAATT<br>GTTGTTGTTAACTTGTTTATTGCAGCTTATAAT<br>GGTTACAAATAAAGCAATAGCATCACAAATTT<br>CACAAATAAAGCATTTTTTTCACTGCATTCTAG<br>TTGTGGTTTGTCCAAACTCATCAATGTATCTTA<br>TCATGTCT | 21 |
| Hamster beta-actin promoter & intron | AGTTGGGGACCAAGACAGAACCATAAGCCAGT<br>GGGATAGATCAGAAATGTTCCAGAGGTGGGAT<br>GGGGCCAGAGTGCCTGCCCCTTGAACCGTCCC<br>AGGGACCAGAGGTGACAAAGTGGCAACACAG<br>GTCCTGCCTGGGAATCTGGTCTGCTCCTACTTA<br>GTAAAGCTGCCTGGTGTCACACAAGAGGCCCC<br>CACTTATTCCTGCACCCCTGGTGGTAGGTGGC<br>GTCTTCTCCCCTGCAGCCACCAGGCTCCCCTGA<br>GAACACTGCCGGCAGTCCTCATTGACAGGCAG<br>TATTCGCTCTGCCCCACCCCCACCTGTGAATTG<br>CAGGGCTGGCAGGTCCTCAGGCAGCTGGCAAA<br>CCGCCTGAACAACTGAGAGATACAGGGCCAGG<br>GCCAGGGCAGTCCCGTCCCCCGGAGGCAGGGA<br>GGGGACGTGCTGGGAAAGTTCTCTCTCTCAGG<br>CCCAGGTTGGTGACTGCAGAAGGCTTCTGTCA<br>AATCTCTTTTGTGGGAACCACAGAGTAGCCCT<br>GAACGTGGGGGTGTGCTTCCAGTATACTCTGG<br>GGTCACCCTTTCCATACTGGAGGCCTCTGCAA<br>CTTCAAAATGCTCTGCTACCAACCTAGCACAA<br>GGAAGTTGGTCCAGCCTCCCCACGCAGGGCCA<br>CTGCTGCAGTCCATATATGGACTAAGCCTTCCT<br>TGGTTTCAACACCTACACTCACTGAGCCCCTAC<br>TATGTGTATGCAGAGCCGAGACAGGCCCTGAG<br>CATCTCATCTGAAGCACCCTTCTTGCCTAAATT<br>CAGTTTTCTGTCACTTTCTCCCAGGAGGTGTGT<br>GTCCCTCTAAGCTAAGCCAGGGGTCCCTCACC<br>CCTGCCCCACTCCCATCCCTAGTGTAGGTATCA<br>GCTGAAGAGCTTCCTGAGCAGAACACTCTTGG<br>GTGCTGACATTTTGATAAATAGGCCCATGTTTA<br>GGAGAGCAGGGGTCCGGGGGGGAGATCTT<br>CTCTGGTGGATTGAGGGCTCCAAGAACTACTC<br>TTTGAGCACGCTGCCCCTCCCAGAGTCCCCAC<br>AGCCTCCAGATGGACTAGAACACAGTTCGGCT<br>GTGGCTGCACATAACTAACAGAGGATAGATGG<br>TGGGTCCCAGCCCAACAGTGCCTGGCAATCAC<br>CCAGAGCCACCAGCTAACGGCCTTGGCTTAGT | 22 |

TABLE 4-continued

Nucleotide sequences of each portion of the
expression cassettes/vectors
used to express anti-IL-1R3 antibody

| Portion/region | Sequence | SEQ ID NO: |
|---|---|---|
| | TTTTTGCCTGGGTGTGATCAGGCAGCCCTCCAA<br>AACTGCCCGGACTCCATGACAAGTTTTGCTTGT<br>TCTATAGAGCACAGTTCCTTTCTAGGTCTGGGG<br>CAAGGGACATCGGGAGACATCTTCCTGCAACA<br>GCTCCAGTCACTGGACCACCAGGCTCGCCCTG<br>TCTTTGGTGTGTGGCCCTGAGTCTCCTAAGTGG<br>CCCAAACCTGTGAAGACCCCTCCAACCACAGT<br>TTTGCTTCTAAATTGTACCCCAACACACCTAGC<br>AAATTGAAACCCCACCAGAAGTCCCCCAGATC<br>TGGCTTTCCGGCTATTGCTGGCAAGGGGGAGT<br>GACTCCCGGCCCATTCAATCCAGGCCCCGCGT<br>GTTCCTCAAACAAGAAGCCACGTAAACATAAA<br>CCGAGCCTCCATGCTGACCCTTGCCCATCGAG<br>GTACTCAATGTTCACGTGATATCCACACCCAG<br>AGGGTCCTGGGGTGGGTGCATGAGCCCCAGAA<br>TGCAGGCTTGATAACCGAGACCCTGAATCGGG<br>CAGTGTCCACAAGGGCGGAGGCCAGTCATGCA<br>TGTTCGGGCCTATGGGCCAGCACCCAACGCC<br>AAAACTCTCCATCCTCTTCCTCAATCTCGCTTT<br>CTCTCTCTCTCTCTTTTTTTTTTTTTTTTTTTT<br>TTTTGCAAAAGGAGGGGAGAGGGGGTAAAAA<br>AATGCTGCACTGTGCGGCTAGGCCGGTGAGTG<br>AGCGGCGCGGAGCCAATCAGCGCTCGCCGTTC<br>CGAAAGTTGCCTTTTATGGCTCGAGTGGCCGC<br>TGTGGCGTCCTATAAAACCCGGCGGCGCAACG<br>CGCAGCCACTGTCGAGTCCGCGTCCACCCGCG<br>AGCACAGGCCTTTCGCAGCTCTTTCTTCGCCGC<br>TCCACACCCGCCACCAGGTAAGCAGGGACAAC<br>AGGCCCAGCCGGCCACAGCCCTCCCGTGGGCA<br>GTGACCGCGCTGCAGGGTCGCGGGGGACACTC<br>GGCGCGGACACCGGGGAAGGCTGGAGGGTGG<br>TGCCGGGCCGCGGAGCGGACACTTTCAGATCC<br>AACTTTCAGTCCAGGGTGTAGACCCTTTACAG<br>CCGCATTGCCACGGTGTAGACACCGGTGGACC<br>CGCTCTGGCTCAGAGCACGCGGCTTGGGGGAA<br>CCCATTAGGGTCGCAGTGTGGGCGCTATGAGA<br>GCCGATGCAGCTTTCGGGTGTTGAACCGTATC<br>TGCCCACCTTGGGGGGAGGACACAAGGTCGGG<br>AGCCAAACGCCACGATCATGCCTTGGTGGCCC<br>ATGGGTCTTTGTCTAAACCGGTTTGCCCATTTG<br>GCTTGCCGGGCGGGGGCGCGGCGGGCCCGG<br>CTCGGCCGGGGGGGGCTGGGTTGCCACTGCG<br>CTTGCGCGCTCTATGGCTGGGTATTGGGGCGC<br>GTGCACGCTGGGGAGGGAGCCCTTCCTCTTCC<br>CCCTCTCCCAAGTTAAACTTGCGCGTGCGTATT<br>GAGACTTGGAGCGCGGCCACCGGGGTTGGGCG<br>AGGGCGGGGCCGTTGTCCGGAAGGGGCGGGG<br>TCGCAGCGGCTTCGGGGCGCCTGCTCGCGCTT<br>CCTGCTGGGTGTGGTCGCCTCCCGCGCGCGCA<br>CTAGCCGCCCGCCGGCGGGGCGAAGGCGGGG<br>CTTGCGCCCGTTTGGGGAGGGGCGGAGGCCT<br>GGCTTCCTGCCGTGGGGCCGCCTCCGGACCAG<br>CGTTTGCCTCTTATGGTAATAACGCGGCCGGC<br>CTGGGCTTCCTTTGTCCCCTGAGTTTGGGCGCG<br>CGCCCCTGGCGGCCCGAGGCCGCGGCTTGCC<br>GGAAGTGGGCAGGGCGGCAGCGGCTGCGCCT<br>AGTGGCCCGCTAGTGACCGCGACCCTCTTTTGT<br>GCCCTGATATAGTTCGCCA | |
| ttgCD52 (present<br>only in the heavy<br>chain expression<br>cassette) | TTGGAGCGCTTCCTCTTCCTCCTACTCACCATC<br>AGCCTCCTCGTTTTGGTACAAATACAAACCGG<br>ACTCTCCGGACAAAACGACACCAGCCAAACCA<br>GCAGCCCCTCAGCATCCAGCAACATAAGCGGA<br>GGCATTTTCCTTTTCTTCGTCGCCAACGCCATA<br>ATCCACCTCTTCTGCTTCAGT | 23 |

DNA sequences of expression cassettes/vectors encoding heavy or light chain of anti-ILR13 antibody are shown in Table 4. Vectors encoding heavy chain and light chain polypeptides of anti-IL-1R3 IgG4-P-FALA Ab (aIL-1R3-IgG4) or anti-IL-1R3 IgG1 LALA Ab (aIL-1R3-IgG1) were electroporated in five replicate pools into CHO DXB11 cell line using dihydrofolate reductase (DHFR) selection. The vector carrying the heavy chain also contained a CD52 reporter. Electroporated cells were subjected to two rounds of selection in growth medium containing 5 nM methotrexate (MTX) and 50 nM MTX, respectively. Antibody titers were measured in all five pools after second round of selection.

tion of 3 ng/ml (IL-1 α/ß), 125 ng/ml (IL-33) or 30 ng/ml (IL-36a/ß/γ). Plates were incubated for 24 hours at 37° C./5% $CO_2$. Each condition was tested in technical triplicates. Secreted human IL-8 levels in the supernatant were measured using CisBio HTRF IL8 detection kit (Cat. No 62HIL08PEG) according to the manufacturer's instructions. Fitting curves and EC50 calculation were done using XLfit fitting. Results are summarized in Table 5 below. The anti-IL-1R3-IgG4-P-FALA antibody was compared against the anti-IL-1R3-IgG1-LALA antibody. Both antibodies demonstrated robust activity against the three pathways.

TABLE 5

Inhibition of IL-36, IL-33 and IL-1 pathway in A431 human epithelial carcinoma cell line by anti-IL-1R3 antibody

| Target Protein Name | IL8 release_hIL1 beta Imax % | IL8 release_hIL1 beta rel IC50 in nM | IL8 release_hIL33 Imax % | IL8 release_hIL33 rel IC50 in nM | IL8 release_hIL36g Imax % | IL8 release_hIL36g rel IC50 in nM | IL8 release_hIL1b & hIL36g Imax % | IL8 release_hIL1b & hIL36g rel IC50 in nM | IL8 release_hIL1b & hIL33 & IL36g Imax % | IL8 release_hIL1b & hIL33 & IL36g rel IC50 in nM | Cmax nM |
|---|---|---|---|---|---|---|---|---|---|---|---|
| anti-IL-1R3-huIgG4-(P-FALA) | 91 | 13.40 | 100 | 2.34 | 103 | 0.45 | 96 | 2.38 | 94 | 8.50 | 300 |
| anti-IL-1R3-huIgG1-(LALA) | 96 | 11.00 | 108 | 1.44 | 104 | 0.34 | 98 | 2.74 | 93 | 7.06 | 300 |

FIG. 1 is entitled "50 mM MTX selected pools—7 day batch titers" and shows the pool number and corresponding antibody titer for each of the five pools selected after second round of MTX selection for pools expressing either aIL-1R3-IgG1 or aIL-1R3-IgG4 Ab. As seen in FIG. 1, all five selected pools expressing aIL-1R3-IgG1 antibody produced an antibody titer below 0.1 g/L. Of the five pools selected expressing aIL-1R3-IgG4 antibody, four pools, 1, 2, 3 and 4, produced higher titers of antibody and thus, were viable for clone isolation.

Pools 2 and 4 expressing aIL-1R3-IgG4, were used for clone selection using clone selection tool. Clones were reviewed for clonality and verified clones expanded for evaluation on AMBR (cell line screening software). The top 21 clones were evaluated for cell growth, titer, metabolites, and product quality. The lead six clones, selected based on antibody titer, were A136, A155, A101, A61 and B21. "A" clones were from pool 2 and "B" clone was from pool 4. The lead six clones also showed the highest antibody productivity of all clones selected.

Example 3: Inhibition of IL-1α/β, IL33 and IL-36α/β/γ Induced IL-8 Release by Skin-Derived Carcinoma A-431 Cells In vitro potency of the anti-IL-1R3 antibodies to interfere with multiple cytokine activities was tested in A-431 stable cell line for IL8 cytokine release.

A-431 cells were seeded in 384-well black, flat bottom, tissue-culture-treated microplates (Corning #3764) at a cell density of 20,000 cells/well in 20 µl DMEM, 10% heat inactivated FCS medium. Antibodies serially diluted in DMEM, 1% heat inactivated FCS were added immediately in a volume of 5 µl and plates were incubated for 60 minutes at 37° C./5% $CO_2$. Thereafter 5 µl of the respective recombinant human IL-1α/1β, IL33 or IL-36α/36β/36γ (R&D Systems) proteins prepared with DMEM, 1% heat inactivated FCS were added in 5 µl medium to a final concentra- Example 4: Fcγ Receptor Binding Activity of Anti-IL-1R3 Antibody in IgG1-LALA and IgG4-P-FALA Format Human Fcγ-receptors were obtained from R&D systems. Binding studies were performed by surface plasmon resonance (SPR) using Biacore T200 instrumentation. Fcγ receptors were captured on CM5 Sensor Chips using an anti-his capturing antibody, according to the manufacturer's instructions using receptor concentrations of 0.1 µg/ml. Antibodies were flown over the thus captured receptors at 3.0 µM for 300 seconds (Fcγ RI), and 420 seconds (Fcγ RIII), respectively. Afterwards buffer was flown over the chip surface in order to monitor the dissociation of the antibody receptor complexes.

Figure 2A:
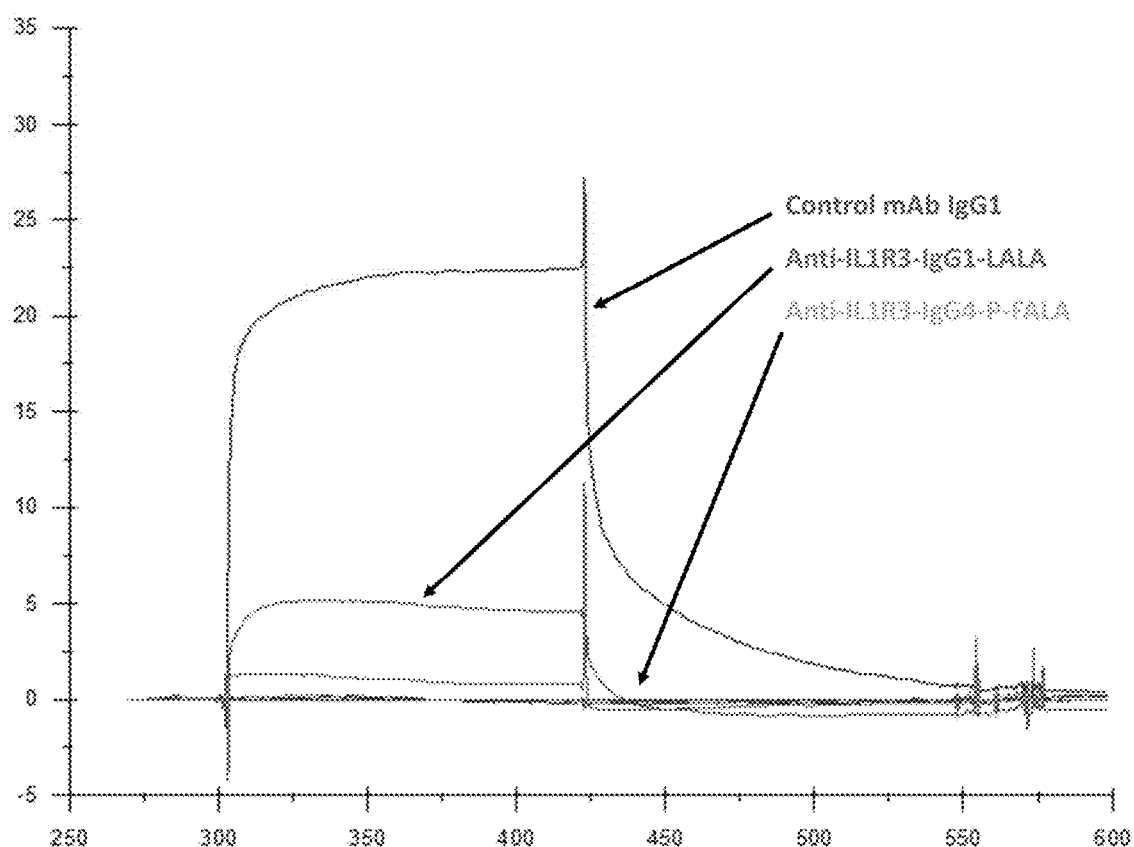
FIGS. 2A-2C show surface plasmon resonance (SPR) sensorgrams that demonstrate that compared to the control (IgG1 antibody), the anti-IL-1R3 antibody in an IgG1-LALA format has residual binding activity to FcγR III (FIGS. 2A and 2B [V176F mutant]) and FcγRI (FIG. 2C) while the same anti-IL-1R3 antibody in an IgG4-P-FALA format has no binding to Fcγ receptor I or III. In all of FIGS. 2A, 2B and 2C the x axis depicts time in seconds (s) and the y axis depicts response in response units (RU) where 0 means the capture baseline.
Figure 2B:
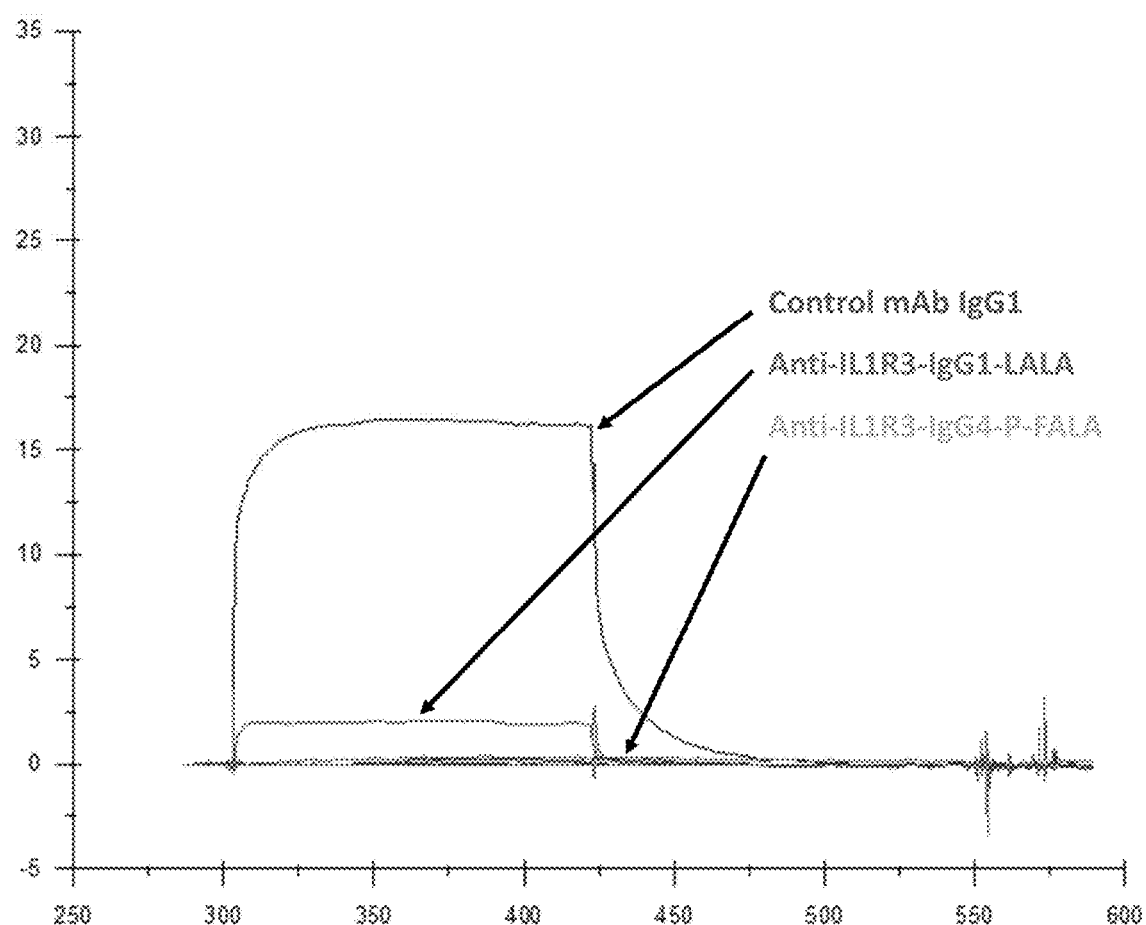

FIG. 2A shows that anti-IL-1R3-IgG1-LALA showed residual binding to human FcγRIIIa and FIG. 2B shows human FcγRIIIa V176F mutant while anti-IL-1R3-IgG4-P-FALA showed no binding.

Figure 2C:
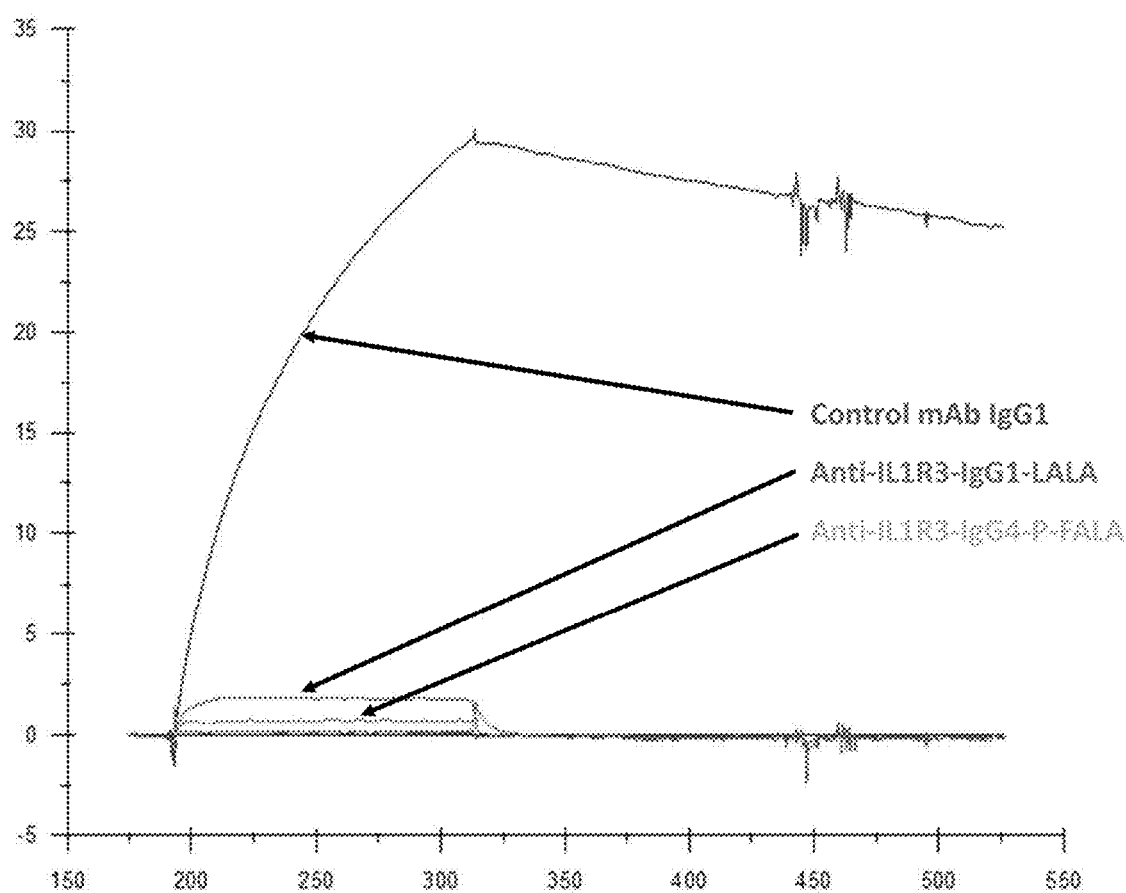

FIG. 2C shows that anti-IL-1R3-IgG1-LALA showed residual binding to human Fcγ RI (CD64) while anti-IL-1R3-IgG4-P-FALA showed no binding.

In all of FIGS. 2A, 2B and 2C the x axis depicts time in seconds (s) and the y axis depicts response in response units (RU) where 0 means the capture baseline.

For cynomolgus receptors, the same trend was observed (data not shown).

For mouse Fcγ receptors, no binding was detected for either anti-IL-1R3-IgG1-LALA or anti-IL-1R3-IgG4-P-FALA (data not shown).

Example 5: Cell Based Antibody-Dependent Cell-Mediated Cytotoxicity (ADCC) of Anti-IL-1R3 Antibody in IgG1-LALA and IgG4-P-FALA Format In antibody-dependent cell-mediated cytotoxicity (ADCC), an effector cell actively lyses a target cell that is bound by a specific antibody. This process starts by the binding of an antibody to the surface of the target cell. Effector cells recognize and bind to the Fc region of the antibody using Fc receptors found on their cell surfaces. Upon binding, the effector cell releases cytotoxic factors that ultimately kill the target cell.

The anti-IL-1R3 antibody in IgG1-LALA and IgG4-P-FALA format was tested for any ADCC activity using a reporter gene assay (iLite ADCC Bioassay #BM5001, SVAR Life Sciences, Malmö). This assay uses reporter-gene-carrying effector cells (Jurkat cells expression FcgammaRIIIa (V158)) that are used in conjunction with target cells that express the specific antigen at constant high levels (i.e. CHO IL1R3 target cells). Binding of the antibody to the target cell and binding of the effector cell to the Fc receptor of the antibody results in expression of the firefly luciferase reporter gene in the effector cell. The promoter of the firefly luciferase in the effector cells includes binding sites for NfkB, AP1, NFAT, CRE and STAT and thus includes the five principal transcription factors of the FcγRIII signal transduction pathway. The effector cells further comprise *Renilla* luciferase for normalization purposes.

Figure 3A:
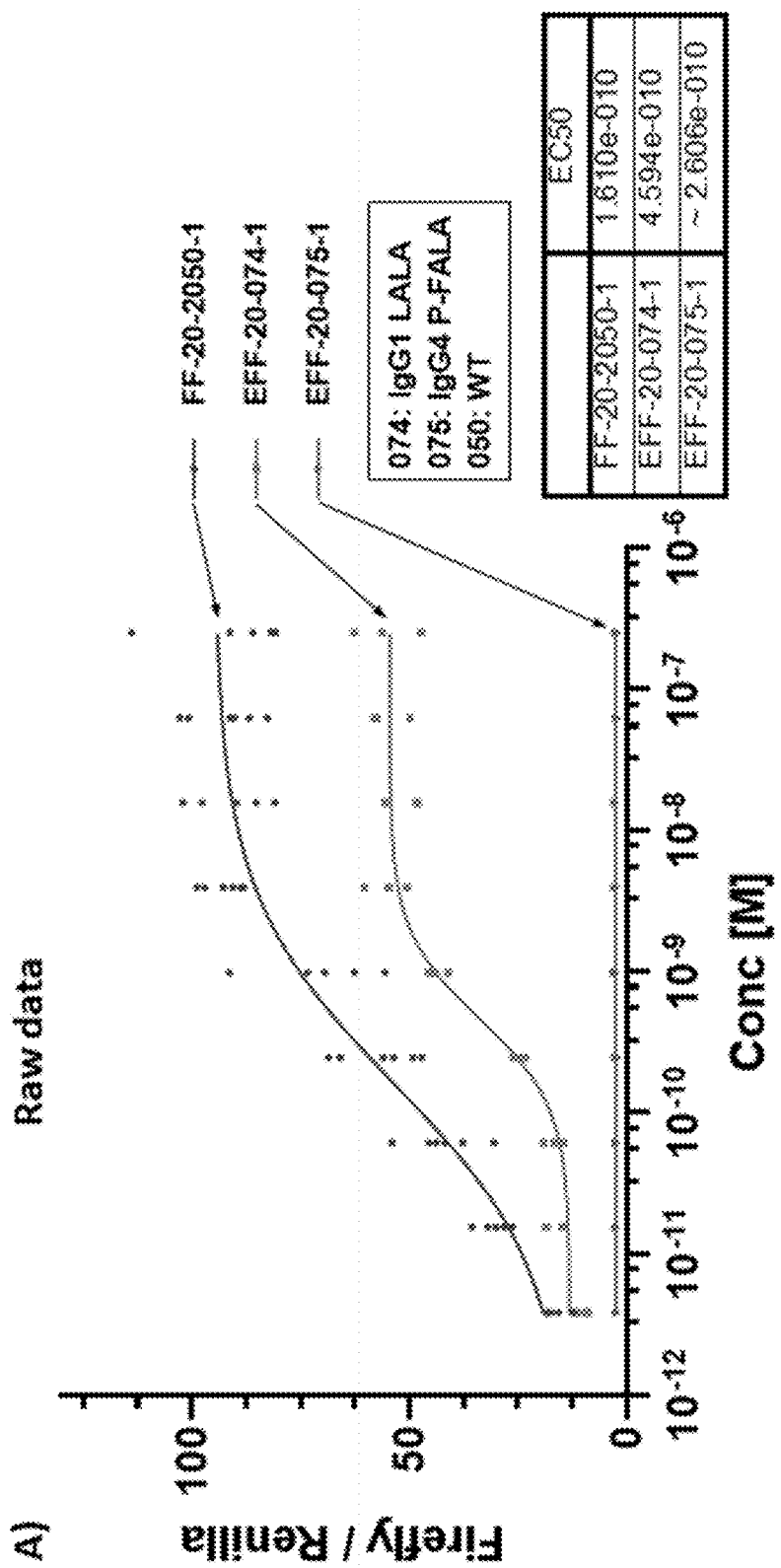
FIGS. 3A-3B show a cell based antibody-dependent cell-mediated cytotoxicity (ADCC) assay that determines the binding of effector cells to the Fc region of an antibody. While the anti-IL-1R3 antibody in an IgG1-LALA format (FIGS. 3A and 3B [EFF-20-074-1]) demonstrated significantly reduced ADCC activity as compared to an IgG1 format (i.e. WT) [FF-20-2050-1], the IgG4-P-FALA format [EFF-20-075-1] resulted in a complete silencing with no binding of effector cells to the Fc receptor.
Figure 3B:
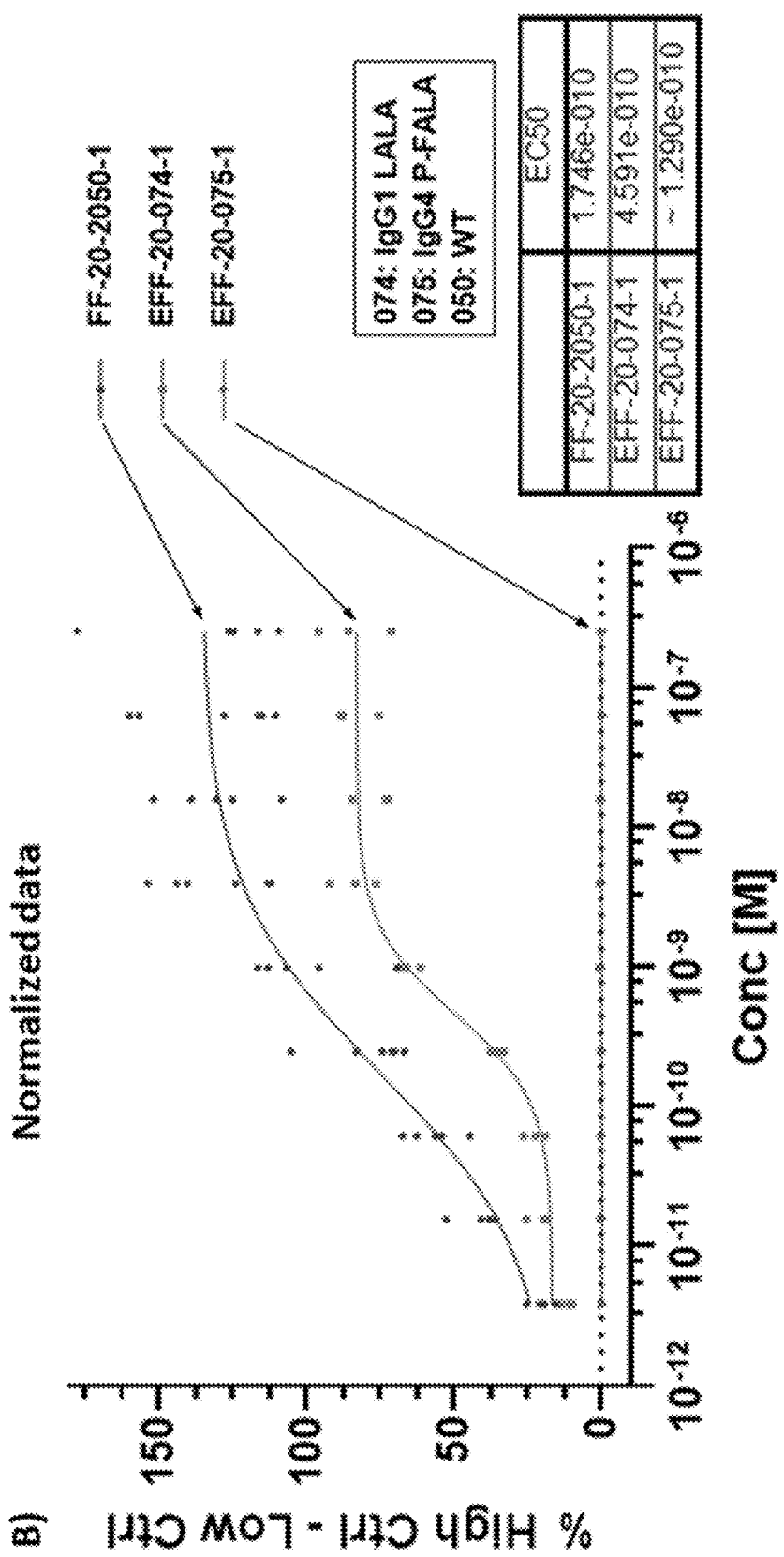

FIG. 3A shows the raw data and FIG. 3B the normalized data of a comparison of the anti-IL-1R3 antibody of the invention in IgG1-LALA and IgG4-P-FALA format as well as an IgG1 control antibody. Whereas the IgG1 control antibody used as a positive control shows strong reporter gene signal indicating ADCC, the IgG1-LALA format significantly reduces the reporter signal. Surprisingly the IgG4-P-FALA format completely abolishes the reporter gene signal indicating the complete absence of Fcγ receptor signaling.

LITERATURE CITED

Angal S, King D J, Bodmer M W, Turner A, Lawson A D, Roberts G, Pedley B, Adair J R. A single amino acid substitution abolishes the heterogeneity of chimeric mouse/human (IgG4) antibody. Mol Immunol. 1993 January; 30(1):105-8. doi: 10.1016/0161-5890(93)90432-b. PMID: 8417368.

Labrijn A. F., Rispens T., Meesters J., Rose R. J., den Bleker T. H., Loverix S., van den Bremer E. T., Neijssen J., Vink T., Lasters I., Aalberse R. C., Heck A. J., van de Winkel J. G., Schuurman J., Parren P. W. (2011) Species-specific determinants in the IgG CH3 domain enable Fab-arm exchange by affecting the noncovalent CH3-CH3 interaction strength. J. Immunol. 187, 3238-3246

Parekh B S, Berger E, Sibley S, Cahya S, Xiao L, LaCerte M A, Vaillancourt P, Wooden S, Gately D. Development and validation of an antibody-dependent cell-mediated cytotoxicity-reporter gene assay. MAbs. 2012 May-June; 4(3):310-8. doi: 10.4161/mabs.19873. Epub 2012 Apr. 26. PMID: 22531445; PMCID: PMC3355484.

Silva J P, Vetterlein O, Jose J, Peters S, Kirby H. The S228P mutation prevents in vivo and in vitro IgG4 Fab-arm exchange as demonstrated using a combination of novel quantitative immunoassays and physiological matrix preparation. J Biol Chem. 2015 Feb. 27; 290(9):5462-9. doi: 10.1074/jbc.M114.600973. Epub 2015 Jan. 7. PMID: 25568323; PMCID: PMC4342462.

What is claimed is:

1. An antibody that specifically binds to IL-1R3, comprising an antibody heavy chain comprising SEQ ID NO: 1 and a light chain comprising SEQ ID NO: 2.

2. A pharmaceutical composition comprising the antibody of claim 1 and a pharmaceutically acceptable diluent, carrier or excipient.

3. An isolated nucleic acid molecule encoding an antibody that specifically binds to IL-1R3,
   wherein the antibody comprises a heavy chain comprising SEQ ID NO: 1 and a light chain comprising SEQ ID NO: 2.

4. An expression vector comprising the nucleic acid molecule of claim 3.

5. A host cell comprising the expression vector of claim 4.

6. The host cell of claim 5, which is a Chinese hamster ovary (CHO) cell.

7. A method of manufacturing an antibody that specifically binds to IL-1R3, comprising the steps of:
   (i) transfecting a host cell using an isolated nucleic acid molecule encoding said antibody or an expression vector comprising a nucleic acid molecule encoding said antibody;
   (ii) cultivating the host cell under conditions allowing expression of the antibody;
   (iii) recovering the antibody; and
   (iv) optionally further purifying and/or modifying and/or formulating the antibody;
   wherein the antibody comprises a heavy chain comprising SEQ ID NO: 1 and a light chain comprising SEQ ID NO: 2.

8. The method of claim 7, wherein the host cell is a Chinese hamster ovary (CHO) cell.

9. The method of claim 7, wherein the method comprises:
   (v) further formulating the antibody,
   wherein the formulating comprises combining the antibody with a pharmaceutically acceptable diluent, carrier or excipient.

10. The method of claim 7, wherein an expression level of the antibody is greater than an expression level of an anti-IL-1R3 antibody comprising a human IgG1 Fc region, wherein the human IgG1 Fc region comprises amino acid substitutions L234A and L235A, according to EU numbering.

11. An antibody produced by the method of claim 7.

12. A method of treating a disease or disorder in a subject in need thereof comprising administering to the subject an effective amount of an antibody that specifically binds to IL-1R3,
    wherein the antibody comprises a heavy chain comprising SEQ ID NO: 1 and a light chain comprising SEQ ID NO: 2,
    wherein the disease or disorder is an autoimmune, autoinflammatory, neoplastic, inflammatory, and/or fibrotic disease or disorder.

13. The method of claim 12 wherein the disease or disorder is a neoplastic disease or disorder.

14. The method of claim 12, wherein the disease or disorder is an inflammatory skin disease.

15. The method of claim 8, wherein the host cell is a CHO DXB11 cell.

16. The method of claim 8, wherein the method comprises:
    (v) further formulating the antibody,
    wherein the formulating comprises combining the antibody with a pharmaceutically acceptable diluent, carrier or excipient.

17. The method of claim 15, wherein the method comprises:
    (v) further formulating the antibody,
    wherein the formulating comprises combining the antibody with a pharmaceutically acceptable diluent, carrier or excipient.

18. The method of claim 8, wherein an expression level of the antibody is greater than an expression level of an anti-IL-1R3 antibody comprising a human IgG1 Fc region, wherein the human IgG1 Fc region comprises amino acid substitutions L234A and L235A, according to EU numbering.

19. The method of claim 15, wherein an expression level of the antibody is greater than an expression level of an anti-IL-1R3 antibody comprising a human IgG1 Fc region, wherein the human IgG1 Fc region comprises amino acid substitutions L234A and L235A, according to EU numbering.

20. An antibody produced by the method of claim 8.
21. An antibody produced by the method of claim 15.
22. The host cell of claim 5, wherein the host cell is a CHO DXB11 cell.

* * * * *

SEQUENCE LISTING

```
Sequence total quantity: 50
SEQ ID NO: 1            moltype = AA  length = 446
FEATURE                 Location/Qualifiers
source                  1..446
                        mol_type = protein
                        organism = synthetic construct
SEQUENCE: 1
EVQLEESGGR LVQPGTSLRL SCAVSGFSLS SYDMSWVRQA PGKGLEWVST IYIGGTTAYA   60
SWPKGRFTIS KTNSKNTLYL QMNSLRAEDT AVYFCARLQG ANYYNSLALW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEAAGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 2            moltype = AA  length = 215
FEATURE                 Location/Qualifiers
source                  1..215
                        mol_type = protein
                        organism = synthetic construct
SEQUENCE: 2
DVQMTQSPSS LSASVGDRVT ITCQASQSIY SFLSWYQQKP GQAPKLLIYA ASDLESGVPS   60
RFSGSGSGTD FTLTISSLQP EDFATYYCQS NYIIDYGAFG QGTKVVIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 3            moltype = AA  length = 120
FEATURE                 Location/Qualifiers
source                  1..120
                        mol_type = protein
                        organism = synthetic construct
SEQUENCE: 3
EVQLEESGGR LVQPGTSLRL SCAVSGFSLS SYDMSWVRQA PGKGLEWVST IYIGGTTAYA   60
SWPKGRFTIS KTNSKNTLYL QMNSLRAEDT AVYFCARLQG ANYYNSLALW GQGTLVTVSS  120

SEQ ID NO: 4            moltype = AA  length = 108
FEATURE                 Location/Qualifiers
source                  1..108
```

```
                           mol_type = protein
                           organism = synthetic construct
SEQUENCE: 4
DVQMTQSPSS LSASVGDRVT ITCQASQSIY SFLSWYQQKP GQAPKLLIYA ASDLESGVPS    60
RFSGSGSGTD FTLTISSLQP EDFATYYCQS NYIIDYGAFG QGTKVVIK                108

SEQ ID NO: 5               moltype = AA  length = 5
FEATURE                    Location/Qualifiers
source                     1..5
                           mol_type = protein
                           organism = synthetic construct
SEQUENCE: 5
SYDMS                                                                 5

SEQ ID NO: 6               moltype = AA  length = 8
FEATURE                    Location/Qualifiers
source                     1..8
                           mol_type = protein
                           organism = synthetic construct
SEQUENCE: 6
GFSLSSYD                                                              8

SEQ ID NO: 7               moltype = AA  length = 16
FEATURE                    Location/Qualifiers
source                     1..16
                           mol_type = protein
                           organism = synthetic construct
SEQUENCE: 7
TIYIGGTTAY ASWPKG                                                    16

SEQ ID NO: 8               moltype = AA  length = 7
FEATURE                    Location/Qualifiers
source                     1..7
                           mol_type = protein
                           organism = synthetic construct
SEQUENCE: 8
IYIGGTT                                                               7

SEQ ID NO: 9               moltype = AA  length = 12
FEATURE                    Location/Qualifiers
source                     1..12
                           mol_type = protein
                           organism = synthetic construct
SEQUENCE: 9
LQGANYYNSL AL                                                        12

SEQ ID NO: 10              moltype = AA  length = 14
FEATURE                    Location/Qualifiers
source                     1..14
                           mol_type = protein
                           organism = synthetic construct
SEQUENCE: 10
ARLQGANYYN SLAL                                                      14

SEQ ID NO: 11              moltype = AA  length = 11
FEATURE                    Location/Qualifiers
source                     1..11
                           mol_type = protein
                           organism = synthetic construct
SEQUENCE: 11
QASQSIYSFL S                                                         11

SEQ ID NO: 12              moltype = AA  length = 6
FEATURE                    Location/Qualifiers
source                     1..6
                           mol_type = protein
                           organism = synthetic construct
SEQUENCE: 12
QSIYSF                                                                6

SEQ ID NO: 13              moltype = AA  length = 7
FEATURE                    Location/Qualifiers
source                     1..7
                           mol_type = protein
                           organism = synthetic construct
SEQUENCE: 13
AASDLES                                                               7

SEQ ID NO: 14              moltype =     length =
```

```
SEQUENCE: 14
000

SEQ ID NO: 15           moltype = AA  length = 10
FEATURE                 Location/Qualifiers
source                  1..10
                        mol_type = protein
                        organism = synthetic construct
SEQUENCE: 15
QSNYIIDYGA                                                                  10

SEQ ID NO: 16           moltype = AA  length = 10
FEATURE                 Location/Qualifiers
source                  1..10
                        mol_type = protein
                        organism = synthetic construct
SEQUENCE: 16
QSNYIIDYGA                                                                  10

SEQ ID NO: 17           moltype = AA  length = 228
FEATURE                 Location/Qualifiers
source                  1..228
                        mol_type = protein
                        organism = synthetic construct
SEQUENCE: 17
ESKYGPPCPP CPAPEAAGGP SVFLFPPKPK DTLMISRTPE VTCVVVDVSQ EDPEVQFNWY            60
VDGVEVHNAK TKPREEQFNS TYRVVSVLTV LHQDWLNGKE YKCKVSNKGL PSSIEKTISK           120
AKGQPREPQV YTLPPSQEEM TKNQVSLTCL VKGFYPSDIA VEWESNGQPE NNYKTTPPVL           180
DSDGSFFLYS RLTVDKSRWQ EGNVFSCSVM HEALHNHYTQ KSLSLSLG                       228

SEQ ID NO: 18           moltype = AA  length = 232
FEATURE                 Location/Qualifiers
source                  1..232
                        mol_type = protein
                        organism = Homo sapiens
SEQUENCE: 18
EPKSCDKTHT CPPCPAPELL GGPSVFLFPP KPKDTLMISR TPEVTCVVVD VSHEDPEVKF            60
NWYVDGVEVH NAKTKPREEQ YNSTYRVVSV LTVLHQDWLN GKEYKCKVSN KALPAPIEKT           120
ISKAKGQPRE PQVYTLPPSR DELTKNQVSL TCLVKGFYPS DIAVEWESNG QPENNYKTTP           180
PVLDSDGSFF LYSKLTVDKS RWQQGNVFSC SVMHEALHNH YTQKSLSLSP GK                  232

SEQ ID NO: 19           moltype = DNA  length = 1398
FEATURE                 Location/Qualifiers
source                  1..1398
                        mol_type = other DNA
                        organism = synthetic construct
SEQUENCE: 19
atgggctggt cctgcatcat cctgtttctg gtggctaccg ctaccggcgt gcactctgaa            60
gtgcagctgg aagaatctgg cggcagactg gtgcagcctg gcacatctct gagactgtct          120
tgtgccgtgt ccggcttctc cctgtcctcc tacgatatgt cctgggtccg acaggctcct          180
ggcaaaggac tggaatgggt gtccaccatc tacatcggcg aacaaccgc ctacctgcag           240
tggcctaagg gcagattcac catctccaag accaactcca gaacaccct gtacctgcag           300
atgaactccc tgagagccga ggataccgcc gtgtacttct cgctagact gcagggcgcc           360
aactactaca actctctggc tctgtggggc agggcacac tggttacagt gtcctccgct           420
tccaccaagg gaccctctgt gtttcctctg gctcctttgct ccagatccac ctccgagtct         480
acagctgctc tgggctgcct ggtcaaggac tactttcctg agcctgtgac cgtgtcctgg          540
aactctggcg ctctgacatc tggcgtgcac acctttccag ctgtgctgca gtcctccggc          600
ctgtactctc tgtcctctgt cgtgaccgtg ccttcctcta gctgggcac aagacctac            660
acctgtaatg tggaccacaa gccttccaac accaaggtga aagcgcagt ggaatctaag           720
tacgccctc cttgtcctcc atgtcctgct ccagaagctg ctggcggcc atcagtgtt            780
ctgttccctc caaagcctaa ggacaccctg atgatctctc ggacccctga agtgacctgc          840
gtggtggtgg atgtgtccca gaaggatccc gaggtgcagt tcaattggta cgtggacggc          900
gtggaagtgc acaacgctaa gaccaagcct agagaggaac agttcaactc cacctacaga          960
gtggtgtccg tgctgaccgt gctgcatcag gattggctga acggcaaaga gtacaagtgc         1020
aaggtgtcca acaagggcct gccttccagc atcgaaaaga ccatcagcaa ggccaagggc         1080
cagcctaggg aacccaggt ttacaccctg cctccaagcc aagaggaaat gaccaagaac          1140
caggtgtccc tgacctgcct cgtgaaggc ttcacccctt ccgatatcgc cgtggaatgg         1200
gagagcaatg gccagcctga gaacaactac aagacaaccc ctcctgtgct ggactccgac         1260
ggcagcttct tcctgtattc ccgcctgacc gtggacaagt ccagatggca gagggcaac         1320
gtgttctcct gctccgtgat gcacgaggcc ctgcacaatc actacaccca gaagtccctg         1380
tctctgtccc tgggctaa                                                      1398

SEQ ID NO: 20           moltype = DNA  length = 705
FEATURE                 Location/Qualifiers
source                  1..705
                        mol_type = other DNA
                        organism = synthetic construct
SEQUENCE: 20
atgggctggt cctgcatcat cctgtttctg gtggctaccg ctaccggcgt gcactctgat           60
```

```
gtgcagatga cccagtctcc ttccagcctg tctgcctctg tgggcgacag agtgaccatc    120
acctgtcagg ccagccagtc tatctactcc ttcctgtcct ggtatcagca gaagcccggc    180
caggctccta agctgctgat ctacgctgcc tccgacctgg aatctggcgt gccctctaga    240
ttctccggct ctggctctgg caccgacttt accctgacaa tctccagcct gcagcctgag    300
gacttcgcca cctactactg ccagtccaac tacatcatcg actacggctg ctttggccag    360
ggcaccaagg tggtcatcaa gagaacagtg gccgctcctt ccgtgttcat cttcccacct    420
tccgacgagc agctgaagtc cggcacagct tctgtcgtgt gcctgctgaa caacttctac    480
cctcgggaag ccaaggtgca gtggaaggtg acaatgccc tgcagtccgg caactcccaa    540
gagtctgtga ccgagcagga ctccaaggac agcacctata gcctgtcctc cacactgacc    600
ctgtccaagg ccgactacga aagcacaag tgtacgcct gcgaagtgac ccatcagggc    660
ctgtctagtc ccgtgaccaa gtctttcaac cggggcgagt gttga                   705

SEQ ID NO: 21          moltype = DNA  length = 236
FEATURE                Location/Qualifiers
source                 1..236
                       mol_type = other DNA
                       organism = synthetic construct
SEQUENCE: 21
gatcataatc agccatacca catttgtaga ggttttactt gctttaaaaa acctcccaca     60
cctcccctg aacctgaaac ataaaatgaa tgcaattgtt gttgttaact tgtttattgc    120
agcttataat ggttacaaat aaagcaatag catcacaaat ttcacaaata aagcattttt    180
ttcactgcat tctagttgtg gtttgtccaa actcatcaat gtatcttatc atgtct        236

SEQ ID NO: 22          moltype = DNA  length = 3011
FEATURE                Location/Qualifiers
source                 1..3011
                       mol_type = other DNA
                       organism = synthetic construct
SEQUENCE: 22
agttggggac caagacagaa ccataagcca gtgggataga tcagaaatgt tccagaggtg     60
ggatggggcc agagtgcctg ccccttgaac cgtcccaggg accagaggtg acaaagtggc    120
aacacaggtc ctgcctggga atctggtctg ctcctactta gtaaagctgc ctggtgtcac    180
acaagaggcc cccacttatt cctgcacccc tggtggtagg tggcgtcttc tcccctgcag    240
ccaccaggct cccctgagaa cactgccggc agtcctcatt gacaggcagt attcgctcgg    300
ccccaccccc acctgtgaat tgcagggctg gcaggtcctc aggcagctgg caaaccgcct    360
gaacaactga gagatacagg gccagggcca gggcagtccc gtccccgga ggcagggagg    420
ggacgtgctg ggaaagttct ctctctcagg cccaggttgg tgactgcaga aggcttctgt    480
caaatctctt ttgtgggaac cacagagtag ccctgaacgt ggggtgtgc ttccagtata    540
ctctggggtc accctttcca tactggaggc ctctgcaact tcaaaatgct ctgctaccaa    600
cctagcacaa ggaagttggt ccagcctccc cacgcagggc cactgctgca gtccatatat    660
ggactaagcc ttccttggtt tcaacaccta cactcactga gccctacta tgtgtatgca    720
gagccgagac aggccctgag catctcatct gaagcaccct tcttgcctaa attcagtttt    780
ctgtcacttt ctcccaggag gtgtgtgtcc tctaagcta agcagggt ccctcacccc    840
tgccccactc ccatccctag tgtaggtatc agctgaagag cttcctgagc agaacactct    900
tgggtgctga cattttgata aataggccca tgtttaggag agcaggggtc cggggcgggg    960
agatcttctc tggtggattg agggctccaa gaactactct tgagcacgc tgcccctccc   1020
agagtcccca cagcctccag atggactaga acacagttcg gcgtggctg cacataacta   1080
acagaggata gatggtgggt cccagcccaa cagtgcctgg caatcaccca gagccaccag   1140
ctaacggcct tggcttagtt ttttgcctgg gtgtgatcag gcagccctcc aaaactgccc   1200
ggactccatg acaagttttg cttgttctat agagcacagt tccttctag gtctgggca    1260
agggacatcg ggagacatct tcctgcaaca gctccagtca ctggaccacg aggctcgccc   1320
tgtctttggt gtgtggccct gagtctccta agtggcccaa acctgtgaag accccctcaa   1380
ccacagtttt gcttctaaat tgtacccaa cacacctagc aaattgaaac cccaccagaa   1440
gtcccccaga tctggctttc cggctattgc tggcaagggg gagtgactcc cggcccattc   1500
aatccaggcc ccgcgtgttc tcaaacaag aagccacgta aacataaacc gagcctccat   1560
gctgaccctt gcccatcgag gtactcaatg ttcacgtgat atccacaccc agagggtcct   1620
gggtggggtg catgagcccc agaatgcagg cttgataacc gagaccctga atcgggcagt   1680
gtccacaagg gcggaggcca gtcatgcatg ttcgggccta ggggccagc acccaacgcc   1740
aaaactctcc atcctcttcc tcaatctcgc ttttctctct tctctctttt tttttttttt   1800
tttttttttt ttgcaaaagg aggggagagg gggtaaaaaa atgctgcact gtgcggctag   1860
gccggtgagt gagcggcgcg gagccaatca gcgctcgccg ttcgaaagt tgcctttat    1920
ggctcgagtg gccgctgtgg cgtcctataa acccggcgg cgcaacgcgc agccactgtc   1980
gagtccgcgt ccacccgcga gcacaggcct ttcgcagctc tttcttcgcc gctccacacc   2040
cgccaccagg taagcaggga caacaggccc agccgccccg tgggcagtga   2100
ccgcgctgca gggtcgcggg ggacactcgg cgcggacacc ggggaaggct ggagggtggt   2160
gccgggccgc ggagcggaca ctttcagatc caactttcag tccagggtgt agacccttta   2220
cagccgcatt gccacggtgt agacaccggt ggacccgctc tggctcagag cacgcggctt   2280
ggggggaaccc attagggtcg cagtgtgggc gctatgagag ccgatgcaga tttcgggtgt   2340
tgaaccgtat ctgcccacct tgggggagg acacaaggtc gggagccaaa cgccacgatc   2400
atgccttggt ggcccatggg tctttgtcta aaccggtttg cccatttggc ttgccgggcg   2460
ggcgggcgcg gcgggcccgg ctcgccgggg gggggctgg gttgccactg cgcttgcgcg   2520
ctctatggct gggtattggg gcgcgtgcac gctggggagg gagcccttcc tcttcccct   2580
ctcccaagtt aaacttgcgc gtgcgtattg agacttggag cgcggccacc ggggttgggc   2640
gagggcgcgg ccgttgtccg gaaggggcgg ggtgcgaggc gttcgggcg gcctgctcgc   2700
gcttcctgct gggtgtggtc gcctcccgcg cgcgcactag ccgccgccg cggggccgaa   2760
ggcgggggctt cgcccgttt gggagggggg cgaggcctg gcttcctgcc gtggggccgc   2820
ctccggacca gcgtttgcct cttatggtaa taacgcggcc ggctgggct tcctttgtcc   2880
cctgagtttg ggcgcgcgcc cctggcggc ccgaggccgc ggcttgccgg aagtgggcag   2940
ggcggcagcg gctgcgccta gtggcccgct agtgaccgcg accctctttt gtgccctgat   3000
```

```
                                       -continued
atagttcgcc a                                                           3011

SEQ ID NO: 23           moltype = DNA   length = 183
FEATURE                 Location/Qualifiers
source                  1..183
                        mol_type = other DNA
                        organism = synthetic construct
SEQUENCE: 23
ttggagcgct tcctcttcct cctactcacc atcagcctcc tcgttttggt acaaatacaa      60
accggactct ccggacaaaa cgacaccagc caaaccagca gccccctcagc atccagcaac    120
ataagcggag gcattttcct tttcttcgtc gccaacgcca taatccacct cttctgcttc    180
agt                                                                   183

SEQ ID NO: 24           moltype = AA   length = 117
FEATURE                 Location/Qualifiers
source                  1..117
                        mol_type = protein
                        organism = synthetic construct
SEQUENCE: 24
QVQLQQSGPE LLKPGASVKI SCKASGYAFS SSWMNWVKQR PGKGLEWIGR IYPGDGNTHY      60
SGKFKGKATL TADKSSSIAY MQLSSLTSED SAVYFCGEGY LDPMDYWGQG TSVTVSS        117

SEQ ID NO: 25           moltype = AA   length = 117
FEATURE                 Location/Qualifiers
source                  1..117
                        mol_type = protein
                        organism = synthetic construct
SEQUENCE: 25
QVQLVQSGAE VKKPGSSVKV SCKASGYAFS SSWMNWVRQA PGQGLEWMGR IYPGDGNTHY      60
AQKFQGRVTL TADKSTSTAY MELSSLRSED TAVYYCGEGY LDPMDYWGQG TLVTVSS        117

SEQ ID NO: 26           moltype = AA   length = 117
FEATURE                 Location/Qualifiers
source                  1..117
                        mol_type = protein
                        organism = synthetic construct
SEQUENCE: 26
QVQLVQSGAE VKKPGSSVKV SCKASGYAFT SSWMNWVRQA PGQGLEWMGR IYPGDGNTHY      60
AQKFQGRVTL TADKSTSTAY MELSSLRSED TAVYYCGEGY LDPMDYWGQG TLVTVSS        117

SEQ ID NO: 27           moltype = AA   length = 117
FEATURE                 Location/Qualifiers
source                  1..117
                        mol_type = protein
                        organism = synthetic construct
SEQUENCE: 27
QVQLVQSGAE VKKPGSSVKV SCKASGYTFT SSWMNWVRQA PGKGLEWMGR IYPGDGQTHY      60
AQKFQGRVTL TADKSTSTAY MELSSLRSED TAVYYCGEGY LDPMDYWGQG TLVTVSS        117

SEQ ID NO: 28           moltype = AA   length = 117
FEATURE                 Location/Qualifiers
source                  1..117
                        mol_type = protein
                        organism = synthetic construct
SEQUENCE: 28
QVQLVQSGAE VKKPGSSVKV SCKASGYTFT SSWMNWVRQA PGKGLEWMGR IYPGDGQTHY      60
AQKFQGRVTI TADKSTSTAY MELSSLRSED TAVYYCGEGY LDPMDYWGQG TLVTVSS        117

SEQ ID NO: 29           moltype = AA   length = 108
FEATURE                 Location/Qualifiers
source                  1..108
                        mol_type = protein
                        organism = synthetic construct
SEQUENCE: 29
DIQMTQTTSS LSASLGDRVT ISCSASQGIN NYLNWYQQKP DGTVKLLIHY TSGLHAGVPS      60
RFSGSGSGTD YSLTISNLEP EDVATYYCQQ YSILPWTFGG GTKLEIKR                  108

SEQ ID NO: 30           moltype = AA   length = 108
FEATURE                 Location/Qualifiers
source                  1..108
                        mol_type = protein
                        organism = synthetic construct
SEQUENCE: 30
DIQMTQSPSS LSASVGDRVT ITCSASQGIN NYLNWYQQKP GKAPKLLIHY TSGLHAGVPS      60
RFSGSGSGTD YTLTISSLQP EDVATYYCQQ YSILPWTFGG GTKVEIKR                  108

SEQ ID NO: 31           moltype = AA   length = 108
FEATURE                 Location/Qualifiers
source                  1..108
```

```
                        mol_type = protein
                        organism = synthetic construct
SEQUENCE: 31
DIQMTQSPSS LSASVGDRVT ITCQASQGIN NYLNWYQQKP GKAPKLLIHY TSGLHAGVPS    60
RFSGSGSGTD YTLTISSLEP EDVATYYCQQ YSILPWTFGG GTKVEIKR                 108

SEQ ID NO: 32           moltype = AA   length = 108
FEATURE                 Location/Qualifiers
source                  1..108
                        mol_type = protein
                        organism = synthetic construct
SEQUENCE: 32
DIQMTQSPSS LSASVGDRVT ITCQASQGIN NYLNWYQQKP GKAPKLLIHY TSGLHAGVPS    60
RFSGSGSGTD FTLTISSLEP EDVATYYCQQ YSILPWTFGG GTKVEIKR                 108

SEQ ID NO: 33           moltype = AA   length = 120
FEATURE                 Location/Qualifiers
source                  1..120
                        mol_type = protein
                        organism = synthetic construct
SEQUENCE: 33
QEQLEESGGG LVKPGGTLSL TCTVSGPSLS HFDITWIRQP PGKGLEWIGT ISPGVSTYYA    60
SWAKSRVTIS VDTSLNTVSL KLSSVTAADT ATYFCARGGV GSSWKAFDLW GPGTLVTISS    120

SEQ ID NO: 34           moltype = AA   length = 110
FEATURE                 Location/Qualifiers
source                  1..110
                        mol_type = protein
                        organism = synthetic construct
SEQUENCE: 34
ELVMTQSPSS VSASVGDRVT ITCQASESIS TALAWYQQKP GKAPKLLIYK ASTLPSGVPS    60
RFSGSGSGTD FTLTINSLQP EDFATYYCQQ GFSSGNVHNA FGGGTKVEIK               110

SEQ ID NO: 35           moltype = AA   length = 122
FEATURE                 Location/Qualifiers
source                  1..122
                        mol_type = protein
                        organism = synthetic construct
SEQUENCE: 35
QVQLVQSGAE VKKPGSSVKV SCKASGSPAE PYAIQWVRQA PGQGLEWMGY IIPSLGGYDY    60
AQKFQGRVTI TADESTSTAY MELSSLRSED TAVYYCARGQ TLYESGRQFD IWGQGTLVTV    120
SS                                                                   122

SEQ ID NO: 36           moltype = AA   length = 107
FEATURE                 Location/Qualifiers
source                  1..107
                        mol_type = protein
                        organism = synthetic construct
SEQUENCE: 36
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNNWPWTFGQ GTKVEIK                  107

SEQ ID NO: 37           moltype = AA   length = 124
FEATURE                 Location/Qualifiers
source                  1..124
                        mol_type = protein
                        organism = synthetic construct
SEQUENCE: 37
QVHLQQSGPE LVRPGTSVKI SCEASGYIFL TYWMNWVKQR PGQGLEWIGQ IFPASDSTYY    60
NEMFKDKARF TVDKSSSTAY MQFSSLTSED TAVYFCARSG PYSYYAGGYA LDYWGQGTSV    120
TVSS                                                                 124

SEQ ID NO: 38           moltype = AA   length = 124
FEATURE                 Location/Qualifiers
source                  1..124
                        mol_type = protein
                        organism = synthetic construct
SEQUENCE: 38
QVQLVQSGAE VKKPGSSVKV SCKASGYIFL TYWMNWVRQA PGQGLEWMGQ IFPASGSAYY    60
NQKFKGRVTI TADKSTSTAY MELSSLRSED TAVYYCARSG PYSYYAGGYA LDYWGQGTLV    120
TVSS                                                                 124

SEQ ID NO: 39           moltype = AA   length = 124
FEATURE                 Location/Qualifiers
source                  1..124
                        mol_type = protein
                        organism = synthetic construct
SEQUENCE: 39
QVQLVQSGAE VKKPGSSVKV SCKASGYIFL TYWINWVRQA PGQGLEWMGQ IFPASDSTYY    60
```

```
NQKFKGRVTI TADKSTSTAY MELSSLRSED TAVYYCARSG PYSYYAGGYA LDYWGQGTLV    120
TVSS                                                                124

SEQ ID NO: 40           moltype = AA  length = 124
FEATURE                 Location/Qualifiers
source                  1..124
                        mol_type = protein
                        organism = synthetic construct
SEQUENCE: 40
QVQLVQSGAE VKKPGSSVKV SCKASGYIFL TYWINWVRQA PGQGLEWMGQ IFPASGSAYY    60
AQKFQGRVTI TADKSTSTAY MELSSLRSED TAVYYCARSG PYSYYAGGYA LDYWGQGTLV    120
TVSS                                                                124

SEQ ID NO: 41           moltype = AA  length = 124
FEATURE                 Location/Qualifiers
source                  1..124
                        mol_type = protein
                        organism = synthetic construct
SEQUENCE: 41
QVQLVQSGAE VKKPGSSVKV SCKASGYIFL TYWMNWVRQA PGQGLEWMGQ IFPASGSAYY    60
AQKFQGRVTI TVDKSTSTAY MELSSLRSED TAVYYCARSG PYSYYAGGYA LDYWGQGTLV    120
TVSS                                                                124

SEQ ID NO: 42           moltype = AA  length = 124
FEATURE                 Location/Qualifiers
source                  1..124
                        mol_type = protein
                        organism = synthetic construct
SEQUENCE: 42
QVQLVQSGAE VKKPGSSVKV SCKASGYIFL TYWMNWVRQA PGQGLEWMGQ IFPASGSAYY    60
NQKFKGRVTI TADKSTSTAY MELSSLRSED TAVYYCARSG PYSYYAGGYA LDYWGQGTLV    120
TVSS                                                                124

SEQ ID NO: 43           moltype = AA  length = 124
FEATURE                 Location/Qualifiers
source                  1..124
                        mol_type = protein
                        organism = synthetic construct
SEQUENCE: 43
QVQLVQSGAE VKKPGSSVKV SCKASGYIFL TYWINWVRQA PGQGLEWMGQ IFPASGSTYY    60
NEKFKGRVTI TADKSTSTAY MELSSLRSED TAVYYCARSG PYSYYAGGYA LDYWGQGTLV    120
TVSS                                                                124

SEQ ID NO: 44           moltype = AA  length = 107
FEATURE                 Location/Qualifiers
source                  1..107
                        mol_type = protein
                        organism = synthetic construct
SEQUENCE: 44
DIQMTQSPAS LSASVGETVT ITCRTSENIN SYLAWYQQKQ GKSPQLLVHY AKTLAEGVPS    60
RFSGSGSGTQ FSLKINSLKP EDFGSYYCQH HYGTSLTFGA GTKLELK                 107

SEQ ID NO: 45           moltype = AA  length = 107
FEATURE                 Location/Qualifiers
source                  1..107
                        mol_type = protein
                        organism = synthetic construct
SEQUENCE: 45
DIQMTQSPSS LSASVGDRVT ITCRASQSIS SYLAWYQQKP GKAPKLLIHY AKSLAEGVPS    60
RFSGSGSGTD FTLTISSLQP EDFATYYCQH HYGTSLTFGQ GTKLEIK                 107

SEQ ID NO: 46           moltype = AA  length = 107
FEATURE                 Location/Qualifiers
source                  1..107
                        mol_type = protein
                        organism = synthetic construct
SEQUENCE: 46
DIQMTQSPSS LSASVGDRVT ITCRASQSIS SYLAWYQQKP GKAPKLLIHY AKSLAEGVPS    60
RFSGSGSGTD FTLTISSLQP EDFATYYCQH HYGTSLTFGQ GTKLEIK                 107

SEQ ID NO: 47           moltype = AA  length = 107
FEATURE                 Location/Qualifiers
source                  1..107
                        mol_type = protein
                        organism = synthetic construct
SEQUENCE: 47
DIQMTQSPSS LSASVGDRVT ITCRASQSIS SYLAWYQQKP GKAPKLLIHY AKSLAEGVPS    60
RFSGSGSGTD FTLTISSLQP EDFATYYCQH HYGTSLTFGQ GTKLEIK                 107
```

```
SEQ ID NO: 48          moltype = AA  length = 107
FEATURE                Location/Qualifiers
source                 1..107
                       mol_type = protein
                       organism = synthetic construct
SEQUENCE: 48
DIQMTQSPSS LSASVGDRVT ITCRASQSIS SYLAWYQQKP GKAPKLLIHY ASSLAEGVPS     60
RFSGSGSGTD FTLTISSLQP EDFATYYCQH HYGTSLTFGQ GTKLEIK                  107

SEQ ID NO: 49          moltype = AA  length = 107
FEATURE                Location/Qualifiers
source                 1..107
                       mol_type = protein
                       organism = synthetic construct
SEQUENCE: 49
DIQMTQSPSS LSASVGDRVT ITCRASQSIS SYLAWYQQKP GKAPKLLIHY ASSLAEGVPS     60
RFSGSGSGTD FTLTISSLQP EDFATYYCQH HYGTSLTFGQ GTKLEIK                  107

SEQ ID NO: 50          moltype = AA  length = 107
FEATURE                Location/Qualifiers
source                 1..107
                       mol_type = protein
                       organism = synthetic construct
SEQUENCE: 50
DIQMTQSPSS LSASVGDRVT ITCRASQSIS SYLAWYQQKP GKAPKLLIHY ASSLAEGVPS     60
RFSGSGSGTD FTLTISSLQP EDFATYYCQH HYGTSLTFGQ GTKLEIK                  107
```